United States Patent
Brown et al.

(10) Patent No.: US 9,428,548 B2
(45) Date of Patent: Aug. 30, 2016

(54) ENHANCED PROTEIN PURIFICATION THROUGH A MODIFIED PROTEIN A ELUTION

(75) Inventors: Arick Brown, South San Francisco, CA (US); Christopher J. Dowd, South San Francisco, CA (US); Asha Nandini Radhamohan, South San Fracisco, CA (US)

(73) Assignee: Genentech, Inc., South San Francisco, CA (US)

( * ) Notice: Subject to any disclaimer, the term of this patent is extended or adjusted under 35 U.S.C. 154(b) by 547 days.

(21) Appl. No.: 13/393,525

(22) PCT Filed: Sep. 1, 2010

(86) PCT No.: PCT/US2010/047448
§ 371 (c)(1),
(2), (4) Date: Jul. 16, 2012

(87) PCT Pub. No.: WO2011/028753
PCT Pub. Date: Mar. 10, 2011

(65) Prior Publication Data
US 2013/0041139 A1    Feb. 14, 2013

Related U.S. Application Data

(60) Provisional application No. 61/238,867, filed on Sep. 1, 2009, provisional application No. 61/253,438, filed on Oct. 20, 2009.

(51) Int. Cl.
*C07K 1/22* (2006.01)

(52) U.S. Cl.
CPC ..................... *C07K 1/22* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,515,893 A | 5/1985 | Kung et al. |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,091,178 A | 2/1992 | Hellstrom et al. |
| 5,091,313 A | 2/1992 | Chang |
| 5,122,469 A | 6/1992 | Mather et al. |
| 5,534,615 A | 7/1996 | Baker et al. |
| 5,622,700 A | 4/1997 | Jardieu et al. |
| 5,672,347 A | 9/1997 | Aggarwal et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,736,137 A | 4/1998 | Anderson et al. |
| 2006/0039901 A1 | 2/2006 | Jiao et al. |
| 2007/0072307 A1 | 3/2007 | Godavarti et al. |
| 2008/0164211 A1 | 7/2008 | Lindner et al. |
| 2008/0167450 A1 | 7/2008 | Pan |
| 2008/0193981 A1 | 8/2008 | Fahrner et al. |
| 2010/0331527 A1* | 12/2010 | Davis et al. ............... 530/387.3 |

FOREIGN PATENT DOCUMENTS

| | | |
|---|---|---|
| EP | 0 183 070 A2 | 6/1986 |
| EP | 0 183 070 A3 | 6/1986 |
| EP | 0 183 070 B1 | 6/1986 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 308 936 A2 | 3/1989 |
| EP | 0 308 936 A3 | 3/1989 |
| EP | 0 308 936 B1 | 3/1989 |
| EP | 0 402 226 A1 | 12/1990 |
| EP | 0 420 397 B1 | 4/1991 |
| RU | 2145610 C1 | 2/2000 |
| WO | 87/00195 A1 | 1/1987 |
| WO | 90/03430 A1 | 4/1990 |
| WO | 91/00360 A1 | 1/1991 |
| WO | 92/20373 A1 | 11/1992 |
| WO | 93/04173 A1 | 3/1993 |
| WO | 93/08829 A1 | 5/1993 |
| WO | 95/19181 A1 | 7/1995 |
| WO | 92/23865 A1 | 9/1995 |
| WO | 96/27011 A1 | 9/1996 |
| WO | 96/30046 A1 | 10/1996 |
| WO | 96/40210 A1 | 12/1996 |
| WO | 97/26912 A2 | 7/1997 |
| WO | 97/26912 A3 | 7/1997 |

(Continued)

OTHER PUBLICATIONS

Hows et al. "High-performance liquid chromatography/tandem mass spectrometry assay for the rapid high sensitivity measurement of basal acetylcholine from microdialysates" J. Nueroscience methods 121, (2002) 33-39.*
Fahrner et al. "Industrial purification of pharmaceutical antibodies: development, operation, and validation of chromatography processes", Biotechnology and Genetic Engineeering Reviews, Jul. 18, 2001, pp. 301-327.*
Fahrner et al. "Industrial Purificaiton of Pharmaceutical Antibodies: development, operation, and validation of chromatography processes" Biotechnology and Genetic Engineering Reviews, 18, 2001, pp. 301-327.*
Aruffo et al., "CD44 is the Principal Cell Surface Receptor for Hyaluronate" *Cell* 61:1303-1313 (Jun. 29, 1990).
Barnes and Sato, "Methods for Growth of Cultured Cells in Serum-Free Medium" *Analytical Biochem.* 102:255-270 (1980).

(Continued)

*Primary Examiner* — Daniel E Kolker
*Assistant Examiner* — James Rogers
(74) *Attorney, Agent, or Firm* — Morrison & Foerster LLP

(57) ABSTRACT

The present invention provides methods for purifying a polypeptide comprising a CH2/CH3 region, comprising binding the polypeptide to Protein A and eluting with a pH gradient starting at a low pH.

73 Claims, 21 Drawing Sheets

(56) References Cited

FOREIGN PATENT DOCUMENTS

| | | |
|---|---|---|
| WO | 98/06248 A2 | 2/1998 |
| WO | 98/06248 A3 | 2/1998 |
| WO | 98/23761 A1 | 6/1998 |
| WO | 98/45331 A2 | 10/1998 |
| WO | 98/45331 A3 | 10/1998 |
| WO | 98/51793 A1 | 11/1998 |
| WO | 99/01556 A2 | 1/1999 |
| WO | 99/01556 A3 | 1/1999 |
| WO | 00/75348 A1 | 12/2000 |
| WO | 00/75348 C1 | 12/2000 |
| WO | 01/00245 A2 | 1/2001 |
| WO | 01/00245 A3 | 1/2001 |
| WO | 01/40309 A2 | 6/2001 |
| WO | 01/40309 A3 | 6/2001 |
| WO | 01/40309 C1 | 6/2001 |
| WO | 2008/025747 A1 | 3/2008 |
| WO | WO-2008/085988 A1 | 7/2008 |

OTHER PUBLICATIONS

Berg et al., "Bispecific Antibodies That Mediate Killing of Cells Infected With Human Immunodeficiency Virus of Any Strain" *Proc. Natl. Acad. Sci. USA* 88:4723-4727 (Jun. 1991).

Brennan et al., "Preparation of Biospecific Antibodies by Chemical Recombination of Monoclonal Immunoglobulin G1 Fragments" *Science* 229(4708):81-83 (Jul. 5, 1985).

Brodeur et al. *Monoclonal Antibody Production Techniques and Applications*, Lawrence B. Schook, New York: Marcel Dekker, Inc.,:55-63 (1987).

Brown et al., "Increasing Parvovirus Filter Throughput of Monoclonal Antibodies Using Ion Exchange Membrane Adsorptive Pre-Filtration" *Biotechnol. Bioeng.* 106(4):627-637 (2010).

Bruggermann et al., "Designer Mice: The Production of Human Antibody Repertoires in Transgenic Animals" *Year Immun* 7:33-40 (1993).

Carter et al., "High Lever *Escherichia coli* Expression and Production of a Bivalent Humanized Antibody Fragment" *Bio/Tech* 10:163-167 (Feb. 1992).

Carter et al., "Humanization of an Anti-p185$^{HER2}$ Antibody for Human Cancer Therapy" *Proc. Natl. Acad. Sci. USA* 89:4285-4289 (May 1992).

Ceriani et al., "Biological Activity of Two Humanized Antibodies Against Two Different Breast Cancer Antigens and Comparison to Their Original Murine Forms" *Cancer Research* 55(23):5852s-5856s (1995).

Chamow et al., "A Humanized, Bispecific Immunoadhesin-Antibody That Retargets CD3$^+$Effectors to Kill HIV-1-Infected Cells" *J Immunol* 153(9):4268-4280 (Nov. 1, 1994).

Choy et al., "Percentage of Anti-CD4 Monoclonal Antibody-Coated Lymphocytes in the Rheumatoid Joint is Associated with Clinical Improvement" *Arthritis Rheum*. 39:52-56 (1996).

Clackson et al., "Making Antibody Fragments Using Phage Display Libraries" *Nature* 352:624-628 (Aug. 15, 1991).

de Wit et al., "Real-Time Quantitative PCR for Retrovirus-Like Particle Quantification in CHO Cell Culture" *Biologicals* 28:137-148 (2000).

Dhainaut et al., "CDP571, a Humanized Antibody to Human Tumor Necrosis Factor—α; Safety, Pharmacokinetics, Immune Response, and Influence of the Antibody of Cytokine Concentrations in Patients with Septic Shock" *Crit. Care Med*. 23(9):1461-1469 (1995).

Duchosal et al., "Immunization of hu-PBL-SCID Mice and the Rescue of Human Monoclonal Fab Fragments Through Combinatorial Libraries" *Nature* 355(6357):258-262 (Jan. 16, 1992).

Ellis et al. "Engineered Anti-CD38 Monoclonal Antibodies for Immunotherapy of Multiple Myeloma," *J. Immunol*. 155(2):925-937, (Jul. 15, 1995).

Goding, *Monoclonal Antibodies: Principles and Practice* "Production and Application of Monoclonal Antibodies in Cell Biology, Biochemistry and Immunology" Academic Press, 56-103 (1986).

Graham et al., "Characteristics of a Human Cell Line Transformed by DNA From Human Adenovirus Type 5" *J. Gen. Virol*. 36(1):59-72 (Jul. 1977).

Graziano et al., "Construction and Characterization of a Humanized Anti-γ-Ig Receptor Type I (FcγRI) Monoclonal Antibody" *J. Immunol*. 155:4996-5002 (1995).

Gruber et al., "Efficient Tumor Cell Lysis Mediated by a Bispecific Single Chain Antibody :Expressed in *Escherichia coli*" *J. Immunol*. 152:5368-5374 (1994).

Ham and McKeehan, "Media and Growth Requirements" *Method Enzymol*. 58:44-93 (1979).

Hollinger et al., ""Diabodies": Small Bivalent and Bispecific Antibody Fragments" *Proc. Natl. Acad. Sci. USA* 90:6444-6448 (Jul. 1993).

Hoogenboom et al., "Construction and Expression of Antibody-Tumor Necrosis Factor Fusion :Proteins" *Molecular Immunology* 28(9):1027-1037 (1991).

Hoogenboom et al., "By-Passing Immunisation. Human Antibodies From Synthetic Repertoires of Germline $V_H$ Gene Segments Rearranged in Vitro" *J. Mol. Biol*. 227:381-388 (1992).

Hourmant et al., "Administration of an Anti-CD11a Monoclonal Antibody in Recipients of Kidney Transplantation" *Transplantation* 58(3):377-380 (Aug. 1994).

Jakobovits et al., "Analysis of Homozygous Mutant Chimeric Mice: Deletion of the Immunoglobulin Heavy-Chain Joining Region Blocks B-cell Development and Antibody Production" *Proc. Natl. Acad. Sci. USA* 90(6):2551-2555 (Mar. 15, 1993).

Jakobovits et al., "Germ-line Transmission and Expression of a Human-Derived Yeast :Artificial Chromosome" *Nature* 362(6417):255-258 (Mar. 18, 1993).

Jones et al., "Replacing the Complementarity-Determining Regions in a Human Antibody with Those From a Mouse" *Nature* 321(6069):522-525 (May 29, 1986).

Jurcic et al., "Radiolabeled Anti-CD33 Monoclonal Antibody M195 for Myeloid Leukemias" *Cancer Research* 55:5908s-5910s (Dec. 1, 1995).

Juweid et al. "Treatment of Non-Hodgkin's Lymphoma with Radiolabeled Murine, Chimeric, or Humanized LL2, an Anti-CD22 Monoclonal Antibody," *Cancer Res*. 55(23 Supp.):5899s-5907s, (Dec. 1, 1995).

Kim et al. et al., "The Vascular Endothelial Growth Factor Proteins: Identification of Biologically Relevant Regions by Neutralizing Monoclonal Antibodies" *Growth Factors*7:53-64 (1992).

Kohler and Milstein, "Continuous Cultures of Fused Cells Secreting Antibody of Predefined Specificity" *Nature* 256:495-497 (Aug. 7, 1975).

Kostelny et al., "Formation of a Bispecific Antibody by the use of Leucine Zippers" *J. Immunol*. :148(5):1547-1553 (Mar. 1, 1992).

Kozbor et al., "A Human Hybrid Myeloma for Production of Human Monoclonal Antibodies" *Immunol* 133(6):3001-3005 (Dec. 1984).

Le Doussal et al., "In Vitro and In Vivo Targeting of Radiolabeled Monovalent and Divalent Haptens with Dual Specificity Monoclonal Antibody Conjugates: Enhanced Divalent Hapten Affinity for Cell-Bound Antibody Conjugate" *J. Nucl. Med*. 30:1358-1366 ( 1989).

Lindmark et al., "Binding of Immunoglobulins to Protein A and Immunoglobulin Levels in Mammalian Sera" *J. Immonol. Methods* 62:1-13 (1983)

Litton et al., "Antibody-Targeted Superantigen Therapy Induces Tumor-Infiltrating Lymphocytes, Excessive Cytokine Production, and Apoptosis in Human Colon Carcinoma" *Eurpoean Journal of Immunology* 26:1-9 (1996).

Lorenz, H. et al., "In Vivo Blockade of TNF-αby Intravenous Infusion of a Chimeric Monoclonal TNF-α Antibody in Patients with Rheumatoid Arthritis" *J. Immunol*. 156:1646-1653 (1996).

Marks et al., "By-Passing Immunization. Human Antibodies From V-Gene Libraries Displayed on Phage" *J. Mol. Biol*. 222:581-597 (1991).

Marks et al., "By-Passing Immunization: Building High Affinity Human Antibodies by (Chain Shuffling" *Bio/Technology* 10:779-783 (Jul. 1992).

(56) References Cited

OTHER PUBLICATIONS

Mather, "Establishment and Characterization of Two Distinct Mouse Testicular Epithelial Cell Lines" *Biol. Reprod.* 23:243-252 (1980).
McCafferty et al., "Phage Antibodies: Filamentous Phage Displaying Antibody Variable Domain" *Nature* 348:552-554 (Dec. 1990).
Millstein et al., "Hybrid Hybridomas and Their use in Immunohistochemistry" *Nature* 305:537-539 (1983).
Morimoto and Inouye, "Single-Step Purification of F(ab')$_2$ Fragments of Mouse Monoclonal Antibodies (Immunoglobulins G1) by Hydrophobic Interaction High Performance Liquid Chromatography Using TSKgel phenyl-5PW" *J. Biochem. Biophys. Meth.* 24:107-117 (1992).
Morrison et al., "Chimeric Human Antibody Molecules: Mouse Antigen-Binding Domains with Human Constant Region Domains" *Proc. Natl. Acad. Sci. USA* 81:6851-6855 (Nov. 1984).
Presta, "Antibody Engineering" *Curr. Opin. Struc. Biol.* 2:593-596 ( 1992).
Presta et al., "Humanization of an Antibody Directed Against IgE" *J. Immunol.* 151(5):2623-2632 (Sep. 1, 1993).
Recny et al., "*N*-Glycosylation is Required for Human CD2 Immunoadhesion Functions" *J. Biol. Chem.* 267(31):428-434 (Nov. 5, 1992).
Riechmann et al., "Reshaping Human Antibodies for Therapy" *Nature* 332:323-327 (Mar. 24, 1988).
Richman et al., "Radioimmunotherapy for Breast Cancer Using Escalating Fractionated Doses of [131] I-Labeled Chimeric L6 Antibody With Peripheral Blood Progenitor Cell Transfusions" *Cancer Research* 55(23 Suppl):516s-5920s (1995).
Shalaby et al., "Development of Humanized Bispecific Antibodies Reactive With Cytotoxic Lymphocytes and Tumor Cells Overexpressing the *HER2* Protooncogene" *J. Exp. Med.* 175:217-225 (Jan. 1, 1992).
Sharkey et al., "Evaluation of a Complementarity-Determining Region-Grafted (Humanized) Anti-Carcinoembryonic Antigen Monoclonal Antibody in Preclinical Studies" *Cancer Research* 55(23 Suppl):5935s-5945s (1995).
Sims et al., "A Humanized CD18 Antibody Can Block Function Without Cell Destruction" *J. Immunol*151(4):2296-2308 (Aug 15, 1993).
Stamenkovic et al., "The B Lymphocyte Adhesion Molecule CD22 Interacts with Leukocyte Common Antigen CD45RO on T Cells and α2-6 Sialyltransferase, CD75, on B Cells" *Cell* 66:1133-1144 (Sep. 20, 1991).
St. John et al., "Immunologic Therapy for ARDS, Septic Shock, and Multiple-Organ Failure" *Chest* 103:932-943 (1993).
Stoppa et al., "Anti-LFA1 Monoclonal Antibody (25.3) for Treatment of Steroid-Resistant Grade III-IV Acute Graft-Versus-Host Disease" *Transplant International* 4:3-7 (1991).
Traunecker et al., "Bispecific Single Chain Molecules (Janusins) Target Cytotoxic Lymphocytes on HIV Infected Cells" *Embo J.* 10(12):3655-3659 ( 1991).
Tutt et al., "Trispecific F(ab')$_3$ Derivatives that Use Cooperative Signaling Via the TCR/CD3 Complex and CD2 to Activate and Redirect Resting Cytotoxic T Cells" *J. Immunol.* 147(1):60-69 (Jul. 1991).
Urlauba et al., "Isolation of Chinese Hamster Cell Mutants Deficient in Dihydrofolate Reductase Activity" *Proc. Natl. Acad. Sci. USA* 77(7):4216 (Jul. 1980).
Vaughan et al., "Human Antibodies With Sub-Nanomolar Affinities Isolated From a Large Non-immunized Phage Display Library" *Nat. Biotechnol.* 14:309-314 (Mar. 1996).
Velayudhan et al. "Modeling of Purification Operations in Biotechnology: Enabling Process Development, Optimization, and Scale-Up" *Biotechnol. Prog.* 23:68-73 (2007, e-pub. Jan. 4, 2007).
Verhoeyen et al., "Reshaping human antibodies: Grafting an Antilysozyme Activity" *Science* 239:1534-1536 (Mar. 1988).
Waterhouse et al., "Combinatorial Infection and in vivo Recombination: a Strategy for Making Large Phage Antibody Repertoires" *Nucl. Acids Res.* 21(9):2265-2266 (1993).
Zapata et al., "Engineering linear F(ab')$_2$ Fragments for Efficient Production in *Escherichia coli* and Enhanced Antiproliferative Activity" *Protein Eng.* 8(10):1057-1062 (1995).
Duhamel et al., "pH gradient elution of human IgG1, IgG2 and IgG4 from protein A-sepharose," *Journal of Immunological Methods* 31:211-217, (1979).
Martin et al., "Separation of guinea pig IgG subclasses by affinity chromatography on protein A-sepharose," *Journal of Immunological Methods* 52:205-212, (1982).
Pan et al., "Quantitation of soluble aggregates in recombinant monoclonal antibody cell culture by pH-gradient protein A chromatography," *Analytical Biochemistry* 388:273-278, (2009, e-pub. Mar. 4, 2009).
Supplementary European Search Report mailed on Mar. 28, 2014, for European Patent Application No. 10814394.2, filed on Sep. 1, 2010, 19 pages.

* cited by examiner

Figure 7
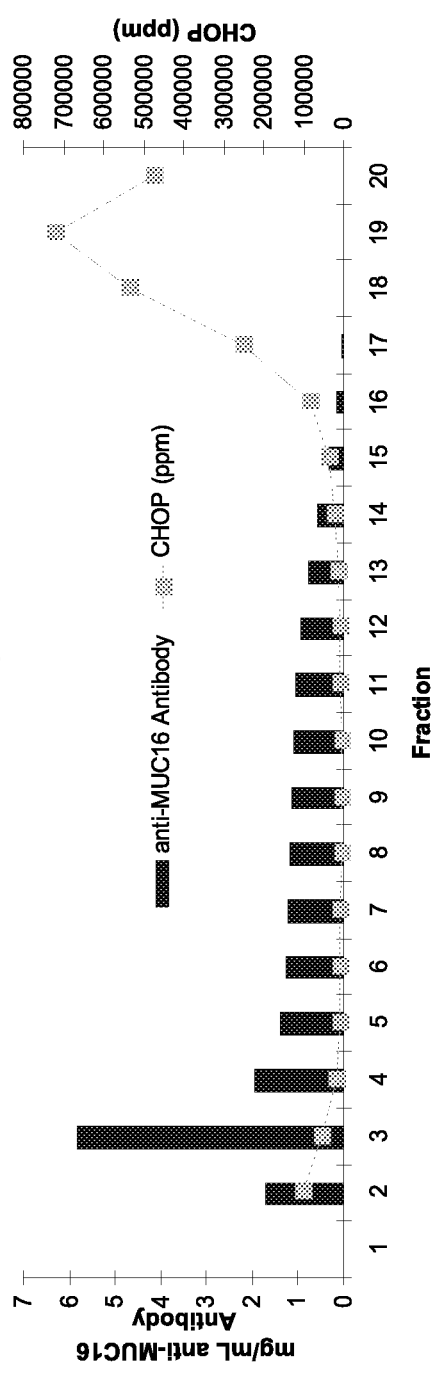
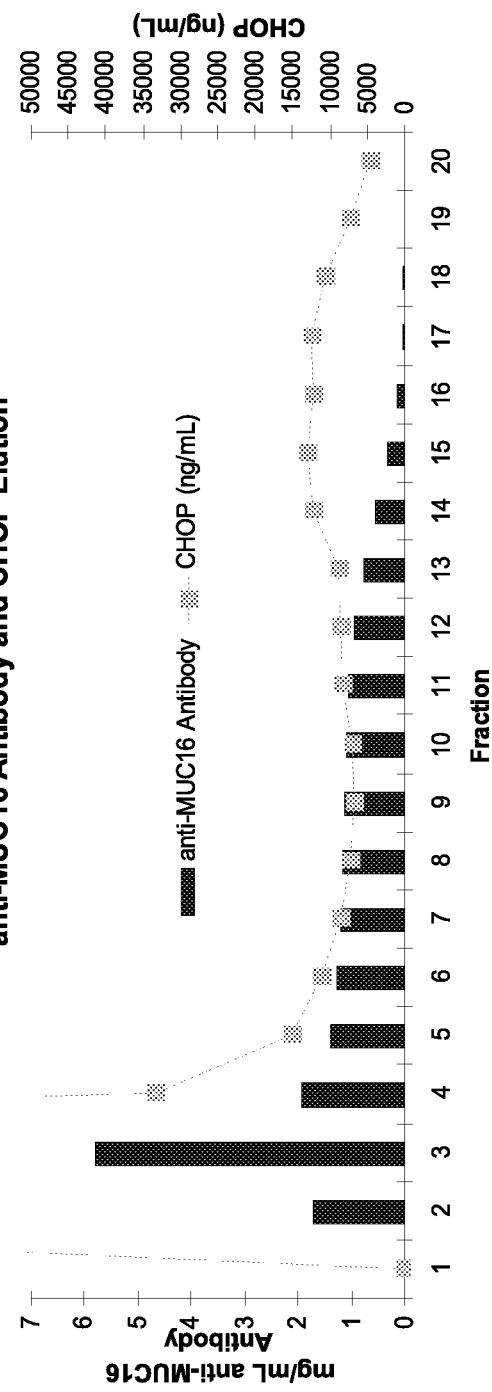

The Pareto Principle:
"80% of the observed behavior can be explained by 20% of the causes"

ENHANCED PROTEIN PURIFICATION THROUGH A MODIFIED PROTEIN A ELUTION

CROSS-REFERENCE TO RELATED APPLICATIONS

This patent application is submitted under 35 U.S.C. §371 as a U.S. national stage application of International Patent Application No. PCT/US2010/047448, filed on Sep. 1, 2010 which claims priority to U.S. Provisional Patent Application No. 61/238,867, filed Sep. 1, 2009 and U.S. Provisional Patent Application No. 61/253,438 filed Oct. 20, 2009, the disclosure of each of which are incorporated herein by reference in their entirety.

FIELD OF THE INVENTION

The field of this invention relates generally to methods for purifying a polypeptide comprising a $C_H2/C_H3$ region, comprising binding the polypeptide to Protein A and eluting with a pH gradient.

BACKGROUND OF THE INVENTION

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. Affinity chromatography, which exploits a specific interaction between the protein to be purified and an immobilized capture agent, is commonly used for some proteins (e.g., proteins for use as a human therapeutic). Protein A is a useful adsorbent for affinity chromatography of proteins, such as antibodies, which contain an Fc region. Protein A is a 41 kD cell wall protein from *Staphylococcus aureas* which binds with a high affinity (about $10^{-8}$ M to human IgG) to the Fc region of antibodies. However, since proteins tend to aggregate or become misfolded, the desired protein (i.e., monomer) is often co-purified with other impurities from these affinity columns, such as protein aggregates, by-products of the cells themselves (i.e., host cell impurities), or virus filter foulant.

Other techniques have been developed to further separate these impurities and mixtures of proteins on the basis of their charge, degree of hydrophobicity, or size, such as ion exchange chromatography, hydrophobic interaction chromatography, or size exclusion chromatography. Several different chromatography resins or sorbents are available for each of these techniques, allowing accurate tailoring of the purification scheme to the particular protein involved. The essence of each of these separation methods is that proteins can be caused either to move at different rates down a long solid phase (e.g., column), achieving a physical separation that increases as they pass further down the solid phase, or to adhere selectively to the separation medium, being then differentially eluted by different solvents. However, each of these methods requires additional buffers, resins or sorbents, and other resources for further purification, and this in turn results in longer processing time and higher cost. Thus, more efficient and economical methods for purifying protein monomers are needed.

Methods of purifying polypeptides from aggregates, multimers, and modified proteins using a protein A column and eluting with a pH gradient elution system was described in U.S. patent application Ser. No. 12/008,160.

All publications, patents, and patent applications cited herein are hereby incorporated by reference herein in their entirety for all purposes to the same extent as if each individual publication, patent, and patent application were specifically and individually indicated to be so incorporated by reference.

BRIEF SUMMARY OF THE INVENTION

The present invention provides methods for purifying a polypeptide comprising a $C_H2/C_H3$ region by binding the polypeptide to Protein A and eluting with a pH gradient starting at a low pH. These purification methods provide the advantages of achieving a better sequential separation of polypeptides or non-aggregates from various impurities, including host cell impurities, virus filter foulants, virus or virus-like particles, basic polypeptide variants, and polypeptide aggregates, and also a higher purity of the desirable polypeptide monomers in the purified fraction/pool. These methods can be achieved using various Protein A chromatography resins and chromatography sorbents. These methods can also be used at manufacturing scale and commercial process, and can facilitate the utilization of alternative downstream purification technologies other than column chromatography.

In one aspect, the invention provides a method for purifying a polypeptide comprising a $C_H2/C_H3$ region, comprising binding the polypeptide to Protein A and eluting with a pH gradient starting at or below 5.0.

In another aspect, the invention provides a method for purifying a polypeptide comprising a $C_H2/C_H3$ region, comprising the steps of: (a) binding the polypeptide to Protein A; and (b) eluting the polypeptide with a pH gradient starting at or below 5.0 using an elution buffer, wherein the elution buffer contains a high pH buffer and a low pH buffer and wherein the pH gradient is formed by adjusting a percentage of each pH buffer in the elution buffer.

In some embodiments, the pH gradient starts at about pH 4.2. In other embodiments, the pH gradient starts at about pH 4.3. In some embodiments, the pH gradient starts at about 4.6. In some embodiments, the pH gradient ends at or above 3.0. In some embodiments, the pH gradient ends at about 3.7.

In some embodiments, the high pH buffer is at about pH 5.0 and wherein the low pH buffer is at about pH 2.7.

In some embodiments, the percentage of low pH buffer starts at about 35%. In some embodiments, the elution buffer containing the low pH buffer at about 35% comprises about 16.25 mM acetate and about 8.75 mM formate. In other embodiments, the percentage of low pH buffer starts at about 25%. In some embodiments, the elution buffer containing the low pH buffer the at about 25% comprises about 18.75 mM acetate and about 6.25 mM formate. In some embodiments, the percentage of low pH buffer starts at about 40%. In some embodiments, the elution buffer containing the low pH buffer at about 40% comprises about 15 mM acetate and about 10 mM formate.

In some embodiments, the polypeptide is loaded with a loading density starting at about 14 g/L. In some embodiments, the polypeptide is loaded with a loading density ranging from about 14 g/L to about 45 g/L.

In some embodiments, the Protein A is a Protein A column chromatography resin or a Protein A chromatography sorbent. In some embodiments, the Protein A chromatography sorbent is a membrane or a monolith.

In some embodiments, the Protein A is a Protein A column chromatography resin and wherein the polypeptide has an elution flow rate ranging from about 5 column volume/hour to about 25 column volume/hour.

In some embodiments, the Protein A is a Protein A column chromatography resin and wherein a purified fraction of the polypeptide contains about or fewer than about 12 Protein A column volumes.

In some embodiments, a host cell impurity is separated from the polypeptide. In some embodiments, the host cell impurity is Chinese Hamster Ovary Protein (CHOP).

In some embodiments, an aggregate is separated from the polypeptide. In other embodiments, a virus filter foulant is separated from the polypeptide.

In some embodiments, a virus particle or a virus-like particle is separated from the polypeptide. In other embodiments, a basic polypeptide variant is separated from the polypeptide.

In some embodiments, the $C_H2/C_H3$ region comprises a Fc region of an immunoglobulin.

In some embodiments, the polypeptide is an antibody. In some embodiments, the antibody is a monoclonal antibody, a polyclonal antibody, a multi-specific antibody, or an antibody fragment.

In other embodiments, the polypeptide is an immunoadhesion.

In some embodiments, the polypeptide has a purity of at least about 98% monomer. In other embodiments, the polypeptide has a purity of at least about 99% monomer.

In some embodiments, the ratio of a host cell impurity to the purified polypeptide is at least about 75% lower, about 80% lower, about 85% lower, about 90% lower, about 95% lower, about 96% lower, about 97% lower, about 98% lower, or about 99% lower than the ratio in unpurified polypeptide.

In some embodiments, a ratio of a host cell impurity to the purified polypeptide is at least about 20% lower than the ratio in a polypeptide purified by a step elution method, wherein the step elution method comprises binding the polypeptide to Protein A and eluting with a pH starting at or below 3.6. In some embodiments, a ratio of a host cell impurity to the purified polypeptide is at least about 60% lower than the ratio in a polypeptide purified by a step elution method, wherein the step elution method comprises binding the polypeptide to Protein A and eluting with a pH starting at or below 3.6.

In some embodiments, the purified polypeptide has virus particle or virus-like particle count less than about 15000 particles/ml. In some embodiments, the purified polypeptide has virus particle or virus-like particle count less than about 12500 particles/ml, less than about 10000 particles/ml, less than about 7500 particles/ml, less than about 5000 particles/ml, less than about 2500 particles/ml, less than about 1500 particles/ml, less than about 1000 particles/ml, less than about 750 particles/ml, less than about 500 particles/ml, less than about 250 particles/ml, less than about 100 particles/ml, or less than about 50 particles/ml. In some embodiments, the virus-like particle is a retrovirus-like particle.

In some embodiments, the purified polypeptide has viral clearance of a virus or a virus-like particle at least about 4 LRV (log 10 reduction of virus). In some embodiments, the purified polypeptide has viral clearance of a virus or a virus-like particle ranging from about 4 LRV to about 8 LRV. In some embodiments, the purified polypeptide has viral clearance of a virus or a virus-like particle ranging from about 4 LRV to about 7 LRV. In some embodiments, the purified polypeptide has viral clearance of a virus or a virus-like particle at about 5 LRV, about 6 LRV, about 7 LRV, or about 8 LRV. In some embodiments, the virus-like particle is a retrovirus-like particle.

In some embodiments, the purified polypeptide is a polypeptide monomer.

In some embodiments, the Protein A is a modified or a non-modified Protein A ligand.

In some embodiments, the purification is a manufacturing scale process.

In some embodiments of any of the aspects of the invention, the purification method further comprises subjecting the polypeptide to a virus filtration step or an ion exchange chromatography step. In some embodiments, the ion exchange chromatography step runs after the purification step.

In some embodiments of any of the aspects of the invention, the purification method does not comprise a further purification step to remove an aggregate.

In some embodiments of any of the aspects of the invention, the purification method does not comprise a further purification step to remove a virus filter foulant.

In some embodiments of any of the aspects of the invention, the purification method does not comprise a further purification step to remove a basic polypeptide variant. In some embodiments of any of the aspects of the invention, the purification method does not comprise a further purification step to remove an acidic polypeptide variant.

In another aspect, the invention provides a polypeptide product purified by the methods described herein.

BRIEF DESCRIPTION OF THE DRAWINGS

FIG. 7 shows the CHOP separation for an anti-MUC16 antibody. The CHOP levels per fraction are expressed in ppm or ng/mL.

DETAILED DESCRIPTION OF THE INVENTION

Figure 1:
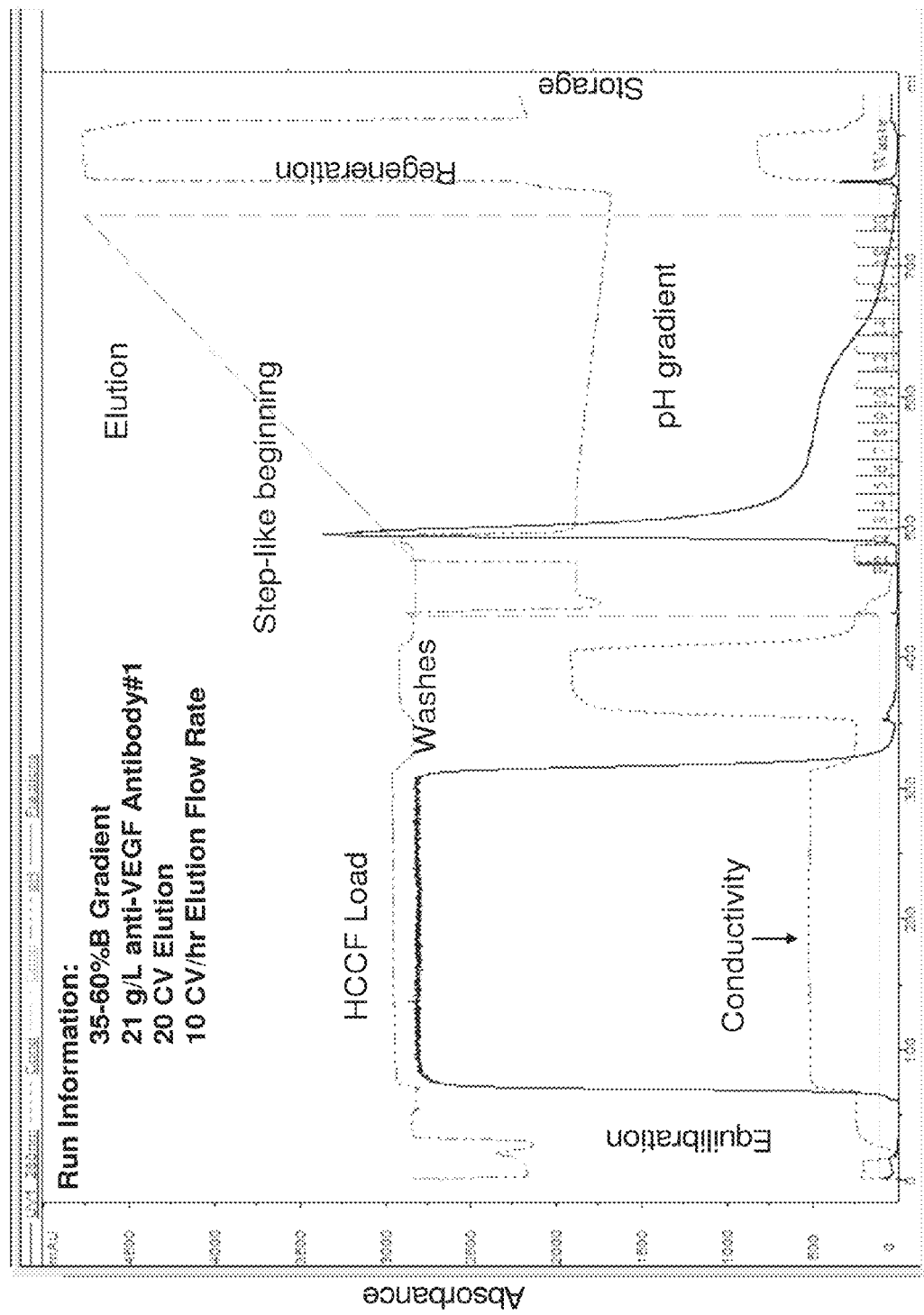
FIG. 1 shows the pH step-gradient chromatogram: x-axis is in mL from start of the Protein A run, and y-axis is absorbance (mAU). The distinctive shape of the step-gradient elution in the UV 280 trace is also shown—large peak is at the start of the elution and is then decreased to a stable height and tapers off at the lower pHs.
Figure 2:
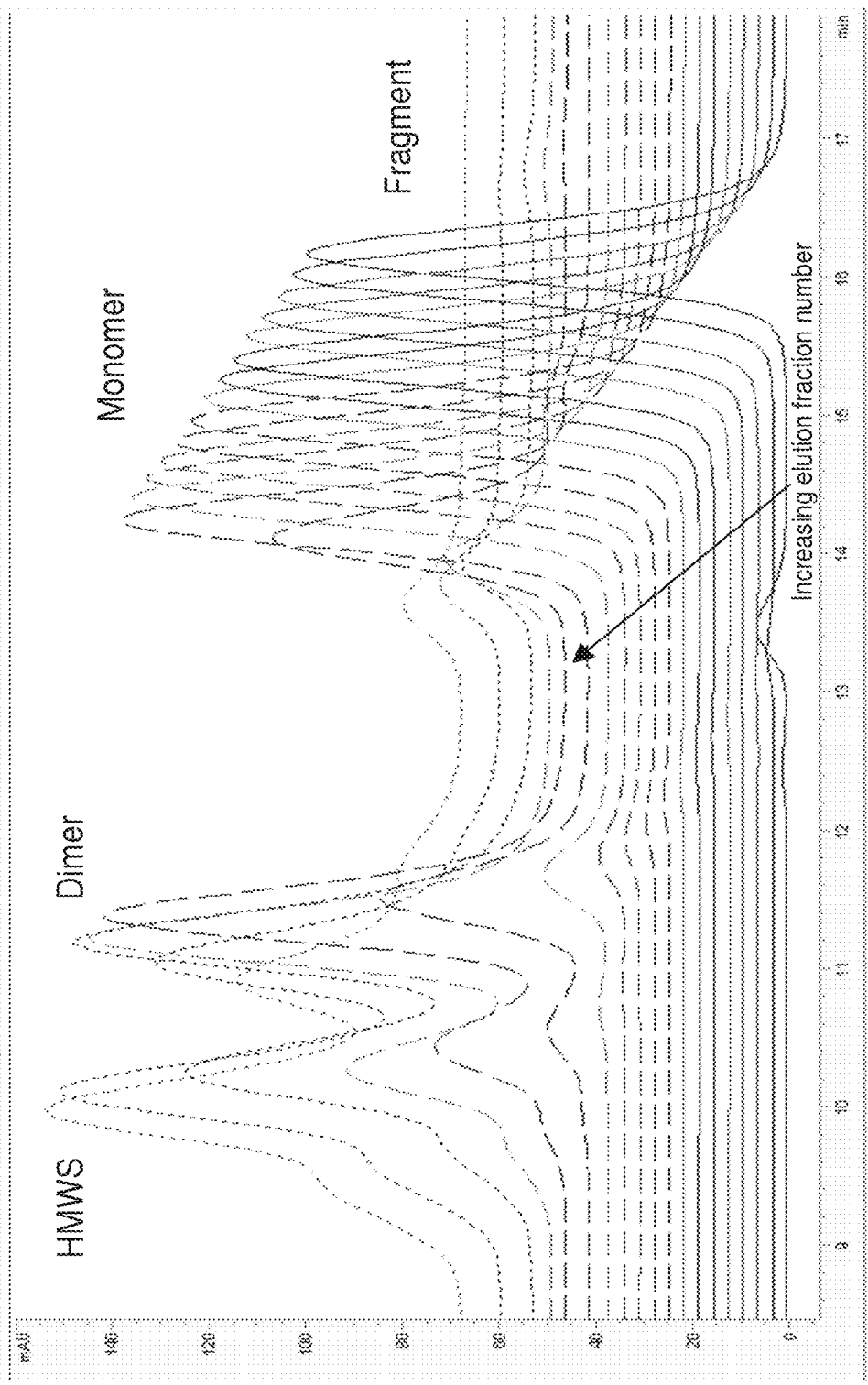
FIG. 2 shows the SEC (Size Exclusion Chromatography) results by fraction of anti-VEGF antibody #1. X-axis is retention time on SEC column (min), Y-axis is normalized UV absorbance (mAU). As fraction number increased (i.e., pH decreases as the gradient elution progresses), the HMWS (High Molecular Weight Species) and dimer peaks (retention times of around 12.5 minutes and 13.5 minutes respectively) also increased while the monomer peak decreases (retention time of 16 minutes). The results from these curves were quantified by integration of all peaks (e.g., HMWS, dimer, and monomer), comparing the separate relative peak areas as percents (e.g., total area was set to 100%, a sample's SEC integration profile could give percents, such as "31% HMWS, 36% dimer, and 33% monomer").
Figure 3:
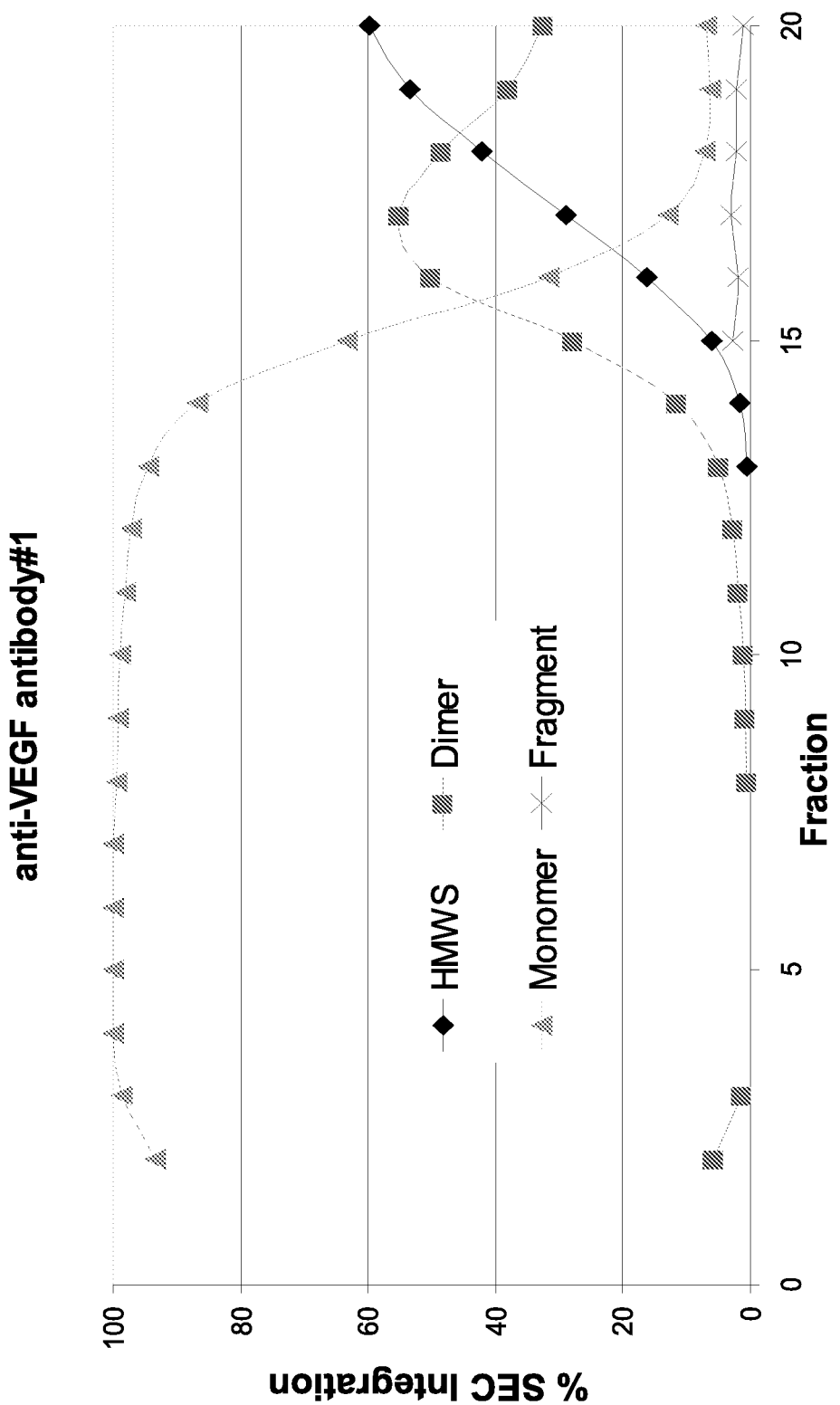
FIG. 3 shows the SEC integration result graph for anti-VEGF antibody #1. This graph shows that the monomer levels were high for the first nine elution fractions with four fractions at 100%, and the dimer and HMWS levels peaked later in the elution. These assay results demonstrate that the pH step-gradient separates aggregates from the monomer of anti-VEGF antibody #1.
Figure 4A:
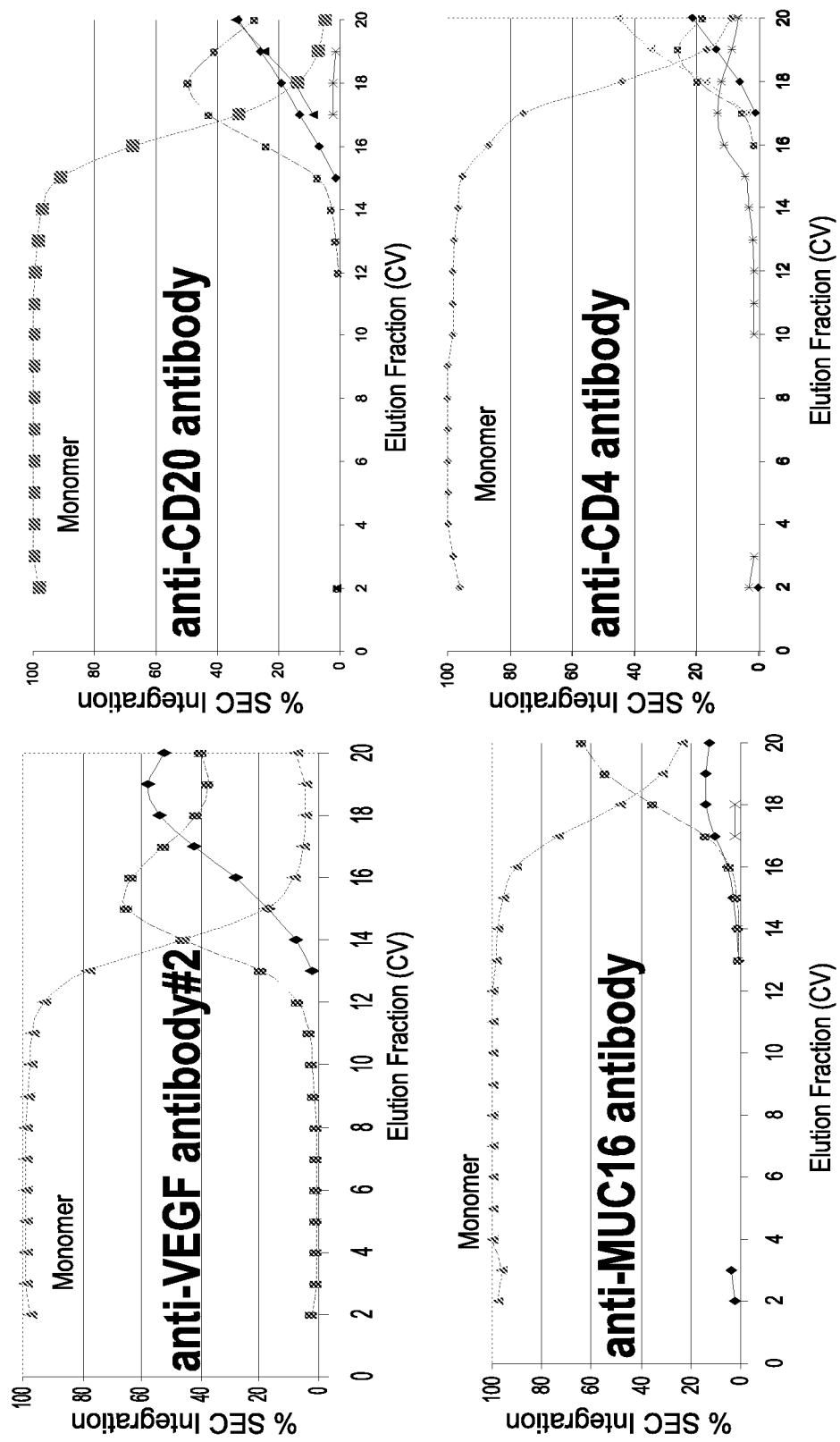
FIG. 4A shows the SEC integration profile for multiple protein molecules (anti-CD20 antibody, anti-VEGF antibody #2, anti-MUC16, and anti-CD4 antibody). The pH step-gradient successfully separated the monomers from aggregates in anti-CD20 antibody, anti-VEGF antibody #2, anti-MUC16, and anti-CD4 antibody.
Figure 4B:
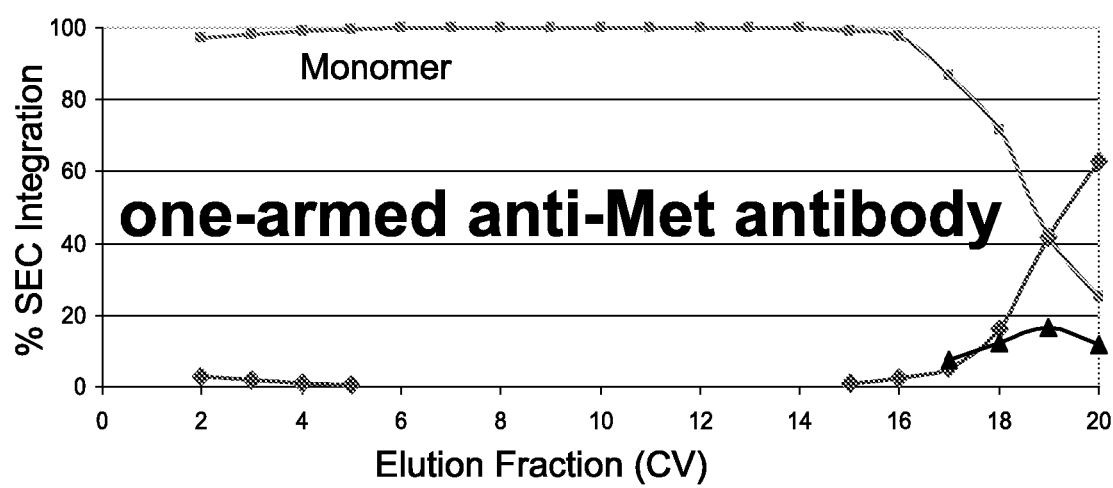
FIG. 4B shows the SEC integration profile for an aglycosylated one-armed anti-Met antibody produced by a bacterial (*E. coli*) host cell fermentation. The pH step-gradient successfully separated monomers from aggregates in the aglycosylated one-armed anti-Met antibody.

The present invention provides methods for purifying a polypeptide comprising a $C_H2/C_H3$ region by binding the polypeptide to Protein A and eluting with a pH gradient starting at a low pH. The inventors have made the striking discovery that eluting polypeptides comprising a $C_H2/C_H3$ region from Protein A with a pH gradient at a low pH can provide a better sequential separation of polypeptides from various impurities, including host cell impurities, virus filter foulants, virus or virus-like particles, basic polypeptide variants, and/or polypeptide aggregates, and also achieve a higher purity or percentage of the desirable polypeptide monomers in the purified fraction/pool. Thus, the invention has significant advantages. The inventors have also discovered that these methods can be achieved using various Protein A chromatography resins and chromatography sorbents and that these methods can be used at manufacturing scale and commercial process and can facilitate the utilization of alternative downstream purification technologies other than column chromatography (e.g., membrane adsorbers).

Accordingly, in one aspect of the invention, provided is a method for purifying a polypeptide comprising a $C_H2/C_H3$ region, comprising binding the polypeptide to Protein A and eluting with a pH gradient starting at or below 5.0.

In another aspect of the invention, provided is a method for purifying a polypeptide comprising a $C_H2/C_H3$ region, comprising the steps of: (a) binding the polypeptide to Protein A; and (b) eluting the polypeptide with a pH gradient starting at or below 5.0 using an elution buffer, wherein the elution buffer contains a high pH buffer and a low pH buffer and wherein the pH gradient is formed by adjusting a percentage of each pH buffer in the elution buffer.

In yet another aspect of the invention, provided is a polypeptide purified by the methods described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

It is understood that the polypeptide of interest herein is one which comprises a $C_H2/C_H3$ region and therefore is amenable to purification by Protein A. The term "$C_H2/C_H3$ region" when used herein refers to those amino acid residues in the Fc region of an immunoglobulin molecule which interact with Protein A. In some embodiments, the $C_H2/C_H3$ region comprises an intact $C_H2$ region followed by an intact $C_H3$ region, and most preferably comprises a Fc region of an immunoglobulin. Examples of $C_H2/C_H3$ region-containing proteins include antibodies, immunoadhesins and fusion proteins comprising a protein of interest fused to, or conjugated with, a $C_H2/C_H3$ region.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the term "purified polypeptide" or "purified protein" is an eluted product from the Protein A affinity chromatography using the pH gradient methods as described herein. Purified polypeptides/proteins preferably contain mostly polypeptide monomers.

As used herein, the term "unpurified polypeptide," "unpurified protein," or "protein load" is a polypeptide or protein in the loading material or starting material prior to the Protein A affinity chromatography purification step.

As used herein, the term "impurity" or "impurities" is a material that is different from the desired polypeptide monomer product. The impurities include, but are not limited to, a polypeptide variant (e.g., acidic or basic polypeptide variant), polypeptide fragment, aggregate or derivative of the desired polypeptide monomer, another polypeptide, lipid, nucleic acid, endotoxin, host cell impurity, or virus filter foulant.

As used herein, the term "monomer(s)" refers to a single unit of a polypeptide comprising a $C_H2/C_H3$ region. For example, in the case of an antibody, a monomer consists of two heavy chains and two light chains; in the case of a one-armed antibody, a monomer consists of one heavy chain and one light chain.

As used herein, the term "basic polypeptide variant" or 'basic variant" refers to a variant of a polypeptide of interest which is more basic (e.g., as determined by cation exchange chromatography) than the polypeptide of interest.

As used herein, the term "acidic polypeptide variant" or 'acidic variant" refers to a variant of a polypeptide of interest which is more acidic (e.g., as determined by cation exchange chromatorgraphy) than the polypeptide of interest.

As used herein, the term "aggregate(s)" refers to any multimers of a polypeptide or a polypeptide fragment comprising a $C_H2/C_H3$ region. For example, an aggregate can be a dimer, trimer, tetramer, or a multimer greater than a tetramer, etc.

As used herein, the term "host cell impurity" refers to any proteinaceous contaminant or by-product introduced by the host cell line, cell cultured fluid, or cell culture. Examples include, but are not limited to, Chinese Hamster Ovary Protein (CHOP), *E. coli*. Protein, yeast protein, simian COS protein, or myeloma cell protein (e.g., NSO protein (mouse plastocytoma cells derived from a BALB/c mouse)).

As used herein, the term "virus filter foulant" refers to any large molecular weight particle or high molecular weight species (HMWS) with a hydrodynamic diameter similar to or greater than the pore size distribution of the parvovirus filter. Virus filter foulants include, but are not limited to, soluble high molecular weight polypeptide aggregates, and soluble and/or insoluble aggregates of host cell impurities (e.g., CHOP).

A "host cell" includes an individual cell or cell culture that can be or has been a recipient for vector(s) for incorporation of polynucleotide inserts to produce polypeptides. Host cells include progeny of a single host cell, and the progeny may not necessarily be completely identical (in morphology or in genomic DNA complement) to the original parent cell due to natural, accidental, or deliberate mutation.

The "solid phase," as used herein, refers to a non-aqueous matrix to which the Protein A can adhere.

A "buffer" is a buffered solution that resists changes in pH by the action of its acid-base conjugate components. Various buffers which can be employed depending, for example, on the desired pH of the buffer are described in *Buffers. A Guide for the Preparation and Use of Buffers in Biological Systems*, Gueffroy, D., Ed. Calbiochem Corporation (1975).

The "equilibration buffer" herein is that used to prepare the solid phase (with immobilized Protein A) for loading the protein of interest.

The "wash buffer" is used herein to refer to the buffer that is passed over the solid phase (with immobilized Protein A) following loading and prior to elution of the protein of interest.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

"Antibody fragments" comprise a portion of a full length antibody, generally the antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments. As used herein, the antibody fragment comprises a $C_H2/C_H3$ region.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5 th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., *J. Immunol. Meth.* 62:1-13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS* (USA) 88:4723-4727 (1991) and Chamow et al., *J. Immunol.* 153:4268 (1994).

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Purification of Polypeptides

The process herein involves purifying a $C_H2/C_H3$ region-containing polypeptide from one or more impurities by Protein A affinity chromatography using a pH gradient starting at a low pH. In one aspect, polypeptide comprising a $C_H2/C_H3$ region can be purified by a method comprising binding the polypeptide to Protein A and eluting with a pH gradient starting at or below 5.0.

In another aspect, polypeptide comprising a $C_H2/C_H3$ region can also be purified by a method comprising the steps of: (a) binding the polypeptide to Protein A; and (b) eluting the polypeptide with a pH gradient starting at or below 5.0 using an elution buffer, wherein the elution buffer contains a high pH buffer and a low pH buffer and wherein the pH gradient is formed by adjusting a percentage of each pH buffer in the elution buffer.

Protein A can be a modified or a non-modified Protein A ligand. As used herein, "Protein A ligand" encompasses native Protein A, Protein A produced synthetically (e.g. by peptide synthesis or by recombinant techniques), and variants thereof which retain the ability to bind proteins which have a $C_H2/C_H3$ region. A modified Protein A ligand can be chemically engineered to be stable in high pH solutions for short amounts of time (e.g., MABSELECT SURE™ (GE Healthcare (Piscataway, N.J.)), POROS® MABCAPTURE™ A (Applied Biosystems (Foster City, Calif.)). The term "non-modified Protein A ligand," as used herein, encompasses Protein A ligand that is similar to Protein A recovered from a native source. Non-modified Protein A ligand, for example, MABSELECT™, PROSEP™ Va, PROSEP™ Ultra Plus, can be purchased commercially from GE Healthcare (Piscataway, N.J.) or Millipore (Billerica, Mass.).

The Protein A can be immobilized on a solid phase. The solid phase may be a purification column, a discontinuous phase or discrete particles, a membrane, or filter. Examples of materials for forming the solid phase include polysaccharides (such as agarose and cellulose) and other mechanically stable matrices such as silica (e.g., controlled pore glass), poly(styrenedivinyl)benzene, polyacrylamide, ceramic particles, and derivatives of any of the above.

Protein A immobilized on a solid phase is used to purify the $C_H2/C_H3$ region-containing polypeptides. In some embodiments, the solid phase is a Protein A column resin comprising a glass bead-based resin, silica-based resin, or agarose-based resin for immobilizing the Protein A. For example, the solid phase is a controlled pore glass column or a silicic acid column. Sometimes, the column has been coated with a reagent, such as glycerol, in an attempt to prevent nonspecific adherence to the column. The PROSEP™ A column is an example of a Protein A controlled pore glass column which is coated with glycerol. In other embodiments, the solid phase is a Protein A chromatography sorbent for immobilizing the Protein A. Protein A chromatography sorbents include, but are not limited to, membranes (e.g. Sartorius (Goettingen, Germany), SARTOBIND™ Protein A membrane) or monoliths (e.g., BIA Separations (Villach, Austria), CIM® Protein A HLD monoliths).

The solid phase for the Protein A chromatography can be equilibrated with an equilibration buffer, and the unpurified polypeptides comprising various impurities (e.g., harvested cell culture fluid) can then be loaded onto the equilibrated solid phase. The polypeptide can be loaded with a loading buffer. Conveniently, the equilibration buffer for equilibrating the solid phase can be the same as the loading buffer, but this is not required. As the polypeptides flow through the solid phase, the polypeptides and various impurities are adsorbed to the immobilized protein A. The wash buffers can be used to remove some impurities, such as host cell impurities, but not polypeptides of interest.

The equilibration buffer is preferably isotonic and commonly has a pH in the range from about 6 to about 8. For example, an equilibration buffer can have 25 mM Tris, 25 mM NaCl, 5 mM EDTA, and pH 7.1.

The "loading buffer" refers to a buffer that is used to load the mixture of the $C_H2/C_H3$ region-containing protein and contaminants onto the solid phase to which the Protein A is immobilized. Often, the equilibration and loading buffers are the same.

The wash buffer may serve to elute cell line impurity or other various impurities. The conductivity and/or pH of the wash buffer is/are such that the impurities are eluted from the Protein A chromatography, but not any significant amounts of the polypeptide of interest.

The polypeptide bound to Protein A can be eluted with a pH gradient using a single elution buffer or a combination of elution buffers.

The "elution buffer" is used to elute the $C_H2/C_H3$ region-containing polypeptide from the immobilized Protein A. As used herein, the elution buffer contains a high pH buffer and a low pH buffer and thereby forms a pH gradient by adjusting a percentage of the high pH buffer and the low pH buffer in the elution buffer. In some embodiments, the elution buffer has a pH in the range from about 3 to about 5. The pH values as used herein are measured without the presence of polypeptides. Examples of pH buffers that control the pH within this range include, but are not limited to, phosphate, acetate, citrate, formic acid, and ammonium buffers, as well as combinations of these. The preferred such buffers are acetate, and formic acid buffers.

In some embodiments, the pH gradient starts at about 5.0. In some embodiments, the pH gradient starts at below 5.0. In some embodiment, the pH gradient starts ranging from about 5.0 to about 4.0. In some embodiments, the pH gradient starts at about 4.9, about 4.8, about 4.7, about 4.6, about 4.5, about 4.4, about 4.3, about 4.2, about 4.1, or about 4.0. In some embodiments, the pH gradient starts at about 4.98, about 4.96, about 4.94, about 4.92, about 4.90, about 4.88, about 4.86, about 4.84, about 4.82, about 4.80, about 4.78, about 4.76, about 4.74, about 4.72, about 4.70, about 4.68, about 4.66, about 4.64, about 4.62, about 4.60, about 4.58, about 4.56, about 4.54, about 4.52, about 4.50, about 4.48, about 4.46, about 4.44, about 4.42, about 4.40, about 4.38, about 4.36, about 4.34, about 4.32, about 4.30, about 4.28, about 4.24, about 4.22, about 4.20, about 4.18, about 4.16, about 4.14, about 4.12, about 4.10, about 4.08, about 4.06, about 4.04, or about 4.02.

In some embodiments, the pH gradient ends at about 3.0. In some embodiments, the pH gradient ends at above 3.0. In some embodiments, the pH gradient ends ranging from about 3.0 to about 4.0. In some embodiments, the pH gradient ends at about 3.1, about 3.2, about 3.3, about 3.4, about 3.5, about 3.6, about 3.7, about 3.8, or about 3.9. In some embodiments, the pH gradient ends at about 3.12, about 3.14, about 3.16, about 3.18, about 3.20, about 3.22, about 3.24, about 3.26, about 3.28, about 3.30, about 3.32, about 3.34, about 3.36, about 3.38, about 3.40, about 3.42, about 3.44, about 3.46, about 3.48, about 3.50, about 3.52, about 3.54, about 3.56, about 3.58, about 3.60, about 3.61, about 3.62, about 3.63, about 3.64, about 3.65, about 3.66, about 3.67, about 3.68, about 3.69, about 3.70, about 3.71, about 3.72, about 3.73, about 3.74, about 3.75, about 3.76, about 3.77, about 3.78, about 3.79, about 3.80, about 3.82, about 3.84, about 3.86, about 3.88, about 3.9, about 3.92, about 3.94, about 3.96, or about 3.98.

In some embodiments, the pH gradient starts at about pH 4.2 and ends at about pH 3.7. In some embodiments, the pH gradient starts at about pH 4.24 and ends at about pH 3.69. For example, anti-VEGF antibodies, anti-CD20 antibodies, anti-MUC16 antibodies, anti-CD4 antibodies, and one armed anti-Met antibodies can be purified using the pH gradient starting at about pH 4.24 and ends at about pH 3.69.

In other embodiments, the pH gradient starts at about pH 4.3 and ends at about pH 3.7. In some embodiments, the pH gradient (i.e., pH step-gradient) starts at about pH 4.34 and ends at about pH 3.69. For example, anti-VEGF antibodies, anti-CD20 antibodies, anti-MUC16 antibodies, anti-CD4 antibodies, and one armed anti-Met antibodies can be purified using the pH gradient starting at about pH 4.34 and ends at about pH 3.69.

In some embodiments, the pH gradient starts at about pH 4.6 and ends at about pH 3.7. In some embodiments, the pH gradient (i.e., pH full-gradient) starts at about pH 4.58 and ends at about pH 3.69. For example, anti-VEGF antibodies, anti-CD20 antibodies, anti-MUC16 antibodies, anti-CD4 antibodies, and one armed anti-Met antibodies can be purified using the pH gradient starting at about pH 4.58 and ends at about pH 3.69.

The elution buffer contains a high pH buffer and a low pH buffer and the pH gradient is formed by adjusting a percentage of each pH buffer in the elution buffer. In some embodiments, the high pH buffer is at about pH 5.0 and the low pH buffer is at about 2.7. For example, the high pH buffer can be 25 mM acetate and pH 5.0, and the low pH buffer can be 25 mM formic acid and pH 2.7.

Adjusting the starting percentage of the low pH buffer can optimize and maximize the purity of the purified polypeptide, and also the sequential separation of the impurities, including aggregates, cell line impurities, basic polypeptide variant, virus particle, virus-like particle, and virus filter foulants, from the polypeptide monomers. The percentage of low pH buffer in the elution buffer can start at about 25%, about 30%, about 35%, about 40%, or about 45%.

In some embodiments, the percentage of low pH buffer in the elution buffer can start at about 25%. In some embodiments, the elution buffer containing the low pH buffer at about 25% comprises about 19 mM acetate, about 6 mM formate, and about 1140 buffer conductivity at pH 4.5-4.6. For example, the elution buffer containing the low pH buffer at about 25% comprises 18.75 mM acetate, 6.25 mM formate, 1141 uS/cm buffer conductivity, at pH 4.58.

In some embodiments, the percentage of low pH buffer in the elution buffer can start at about 35%. In some embodiments, the elution buffer containing the low pH buffer at about 35% comprises about 16 mM acetate, about 9 mM formate, and about 1040 buffer conductivity at pH 4.3-4.4. For example, elution buffer containing the low pH buffer at about 35% comprises 16.25 mM acetate, 8.75 mM formate, 1039 uS/cm buffer conductivity, at pH 4.34.

In some embodiments, the percentage of low pH buffer in the elution buffer can start at about 40%. In some embodiments, the elution buffer containing the low pH buffer at about 40% comprises about 15 mM acetate, about 10 mM formate, and about 974 buffer conductivity at pH 4.2-4.3. For example, the elution buffer containing the low pH buffer at about 40% comprises 15 mM acetate, 10 mM formate, 974 uS/cm buffer conductivity, at pH 4.24.

In some embodiments, the percentage of low pH buffer in the elution buffer can end at about 60%. In some embodiments, the elution buffer containing the low pH buffer at about 60% comprises about 10 mM acetate, about 15 mM formate, and about 763 buffer conductivity at pH 3.6-3.7. For example, the low pH buffer at the end of the pH gradient can be 10 mM acetate, 15 mM formate, 763 uS/cm buffer conductivity, at pH 3.69.

In some embodiments, the elution buffer has a buffer conductivity ranging from about 1200 uS/cm to about 500 uS/cm. In some embodiments, the elution buffer has a buffer conductivity ranging from about 1150 uS/cm to about 700 uS/cm. In some embodiments, the elution buffer has a buffer conductivity of about 1145 uS/cm, about 1141 uS/cm, about 1130 uS/cm, about 1120 uS/cm, about 1110 uS/cm, about 1000 uS/cm, about 1039 uS/cm, about 1000 uS/cm, about 974 uS/cm, about 900 uS/cm, about 800 uS/cm, about 763 uS/cm, or about 700 uS/cm.

In some embodiments, the composition of the elution buffer is about 9-20 mM acetate and 5-15 mM formate. In some embodiments, the composition of the elution is about 10-19 mM acetate and 6-16 mM formate.

Adjusting the loading density of the polypeptide can also optimize and maximize the purity of the purified polypeptide and the separation of the impurities, including aggregates, cell line impurities, basic polypeptide variant, virus particle, virus-like particle, and virus filter foulants, from the polypeptide monomers.

The term "load density" or "loading density" is the density of the purified polypeptide (g) per liter of chromatography resin or the density of the purified polypeptide per liter of membrane/filter volume (L). The loading density is measured in g/L.

In some embodiments, the polypeptide is loaded with a loading density starting at or above 14 g/L. In some embodiments, the polypeptide is loaded with a loading density ranging from about 14 g/L to about 45 g/L or from about 14 g/L to about 70 g/L. In some embodiments, the polypeptide is loaded with a loading density at about 15 g/L, about 17 g/L, about 19 g/L, about 21 g/L, about 23 g/L, about 25 g/L, about 26 g/L, about 27 g/L, about 28 g/L, about 29 g/L, about 31 g/L, about 33 g/L, about 35 g/L, about 37 g/L, about 39 g/L, about 41 g/L, about 43 g/L, about 45 g/L, about 50 g/L, about 55 g/L, about 60 g/L, about 65 g/L, or about 70 g/L.

Adjusting the polypeptide elution residence time (or elution flow rate) can also optimize and maximize polypeptide purity and the sequential separation of impurities from the polypeptide monomers. At increased loading density, the polypeptide elution residence time plays a much larger role in the ability of the pH gradient to fractionate aggregates efficiently. In some embodiments, the polypeptide has an elution flow rate ranging from about 5 column volume/hour to about 35 column volume/hour. In some embodiments, the polypeptide has an elution flow rate ranging from about 5 column volume/hour to about 25 column volume/hour. In some embodiments, the polypeptide has an elution flow rate of about 5 column volume/hour, about 7.5 column volume/hour, about 10 column volume/hour, about 12.5 column volume/hour, about 15 column volume/hour, about 17.5 column volume/hour, about 20 column volume/hour, about 22.5 column volume/hour, about 25 column volume/hour, about 27.5 column volume/hour, about 30 column volume/hour, about 32.5 column volume/hour, or about 35 column volume/hour.

Polypeptides purified using the methods described herein have a yield of at least about any of 75% unpurified polypeptide, 80% unpurified polypeptide, 85% unpurified polypeptide, 90% unpurified polypeptide, 95% unpurified polypeptide, 96% unpurified polypeptide, 97% unpurified polypeptide, 98% unpurified polypeptide, or 99% unpurified polypeptide.

Yield is the total amount of purified polypeptide collected in comparison to the unpurified polypeptide prior to the Protein A affinity chromatography purification as described herein, usually expressed as a percentage of the unpurified polypeptide.

In some embodiments, the ratio of a host cell impurity to the purified polypeptide is at least about 75% lower, about 80% lower, about 85% lower, about 90% lower, about 95% lower, about 96% lower, about 97% lower, about 98% lower, or about 99% lower than the ratio in unpurified polypeptide.

In some embodiments, the ratio of a host cell impurity to the purified polypeptide is at least about 20% lower, about 30% lower, about 40% lower, about 50% lower, about 60% lower, or about 70% lower than the ratio in the polypeptide purified using a pH purification step(s) other than those of the instant invention. For example, in a conventional or typical step Protein A elution method, the polypeptide is purified by binding the polypeptide to Protein A and eluting the polypeptide at or below pH 3.6 without the pH gradient. Accordingly, in some embodiments, the ratio of a host cell impurity to the purified polypeptide is at least about 20% lower, about 30% lower, about 40% lower, about 50% lower, about 60% lower, or about 70% lower than the ratio in a polypeptide purified by a step elution method, wherein the step elution method comprises binding the polypeptide to Protein A and eluting with a pH starting at or below 3.6.

In some embodiments, the ratio of a virus filter foulant to the purified polypeptide is at least about 75% lower, at least about 80% lower, about 85% lower, about 90% lower, about 95% lower, about 96% lower, about 97% lower, about 98% lower, or about 99% lower than the ratio in unpurified polypeptide.

In some embodiments, the ratio of a virus filter foulant to the purified polypeptide is at least about 20% lower, about 30% lower, about 40% lower, about 50% lower, about 60% lower, or about 70% lower than the ratio in the polypeptide purified using a pH purification step(s) other than those of the instant invention. For example, in a conventional or typical step Protein A elution method, the polypeptide is purified by binding the polypeptide to Protein A and eluting the polypeptide at or below pH 3.6 without the pH gradient. Accordingly, in some embodiments, the ratio of a virus filter foulant to the purified polypeptide is at least about 20% lower, about 30% lower, about 40% lower, about 50% lower, about 60% lower, or about 70% lower than the ratio in a polypeptide purified by a step elution method, wherein the step elution method comprises binding the polypeptide to Protein A and eluting with a pH starting at or below 3.6.

In some embodiments, the purified polypeptide has virus particle or virus-like particle count less than about 15000 particles/ml. In some embodiments, the purified polypeptide has virus particle or virus-like particle count less than about 12500 particles/ml, less than about 10000 particles/ml, less than about 7500 particles/ml, less than about 5000 particles/ml, less than about 2500 particles/ml, less than about 1500 particles/ml, less than about 1000 particles/ml, less than about 750 particles/ml, less than about 500 particles/ml, less than about 250 particles/ml, less than about 100 particles/ml, or less than about 50 particles/ml. In some embodiments, the virus-like particle is a retrovirus-like particle.

As used herein, the term "virus particle" is a virion consisting of nucleic acid core surrounded by a protective coat of protein (capsid). "Virus-like particles" are non-infectious virus that resemble similar morphological, biochemical or other properties. They are defective in at least one of the components necessary for virus lifecycle. An example of virus-like particle is a retrovirus-like particle that can not replicate. Virus particle or virus-like particle can be endogenous or exogenous (adventitious). An endogenous virus particle or virus-like particle is produced by a host cell line, present in the cells and cell culture fluid, and can be considered as a host cell impurity. An exogenous or adventitious virus or virus-like particle is not derived from a host cell line.

In some embodiments, the purified polypeptide has viral clearance of a virus or a virus-like particle at least about 4 LRV (log 10 reduction of virus). In some embodiments, the purified polypeptide has viral clearance of a virus or a virus-like particle ranging from about 4 LRV to about 8 LRV. In some embodiments, the purified polypeptide has viral clearance of a virus or a virus-like particle ranging from about 4 LRV to about 7 LRV. In some embodiments, the purified polypeptide has viral clearance of a virus or a virus-like particle at about 5 LRV, about 6 LRV, about 7 LRV, or about 8 LRV. In some embodiments, the virus-like particle is a retrovirus-like particle.

As used herein, the LRV is the difference of log 10 (total virus) in the unpurified polypeptide and in the purified polypeptide.

In some embodiments, the purified polypeptide is a polypeptide monomer.

In some embodiments, a purified fraction of the polypeptide contains about or fewer than about 20 Protein A column volumes. In some embodiments, a purified fraction of the polypeptide contains about or fewer than about 15 Protein A column volumes. In some embodiments, a purified fraction of the polypeptide contains about or fewer than about 12 Protein A column volumes. In some embodiments, a purified fraction of the polypeptide contains about or fewer than about 11, about 10, about 9, about 8, about 7, about 6, about 5.5, or about 5.0 Protein A column volumes.

In some embodiments, the methods described herein remove at least two of the impurities described herein from the desired polypeptide monomer product. For example, the methods remove both an aggregate and a host cell line impurity, both an aggregate and a virus filter foulant, both an aggregate and a virus particle, both an aggregate and a virus-like particle, both an aggregate and a basic polypeptide variant, or a host cell line impurity and a virus particle, etc. In some embodiments, the methods described herein remove at least three of the impurities described herein from the desired polypeptide monomer product. For example, the methods remove an aggregate, a host cell impurity, and a virus filter foulant, or an aggregate, a host cell impurity, and a virus particle, and a basic polypeptide variants, etc. In some embodiments, the methods described herein remove at least four of the impurities described herein from the desired polypeptide monomer product. For example, the methods remove an aggregate, a host cell impurity, a virus filter foulant, and a virus particle, or an aggregate, a host cell impurity, a virus filter foulant, and a virus-like particle. In some embodiments, the methods described herein remove at least five of the impurities described herein from the desired polypeptide monomer product. For example, the methods remove an aggregate, a host cell impurity, a virus filter foulant, a virus particle, and a virus-like particle, etc. In some embodiments, the methods described herein remove all of the impurities from the desired polypeptide product.

In some embodiments, the methods described herein do not comprise a further purification step to remove an aggregate, and the purified polypeptides have a purity of at least about 98% or about 99% monomer. Aggregate clearance normally performed on a separate ion exchange chromatography step is not required following the Protein A chromatography using the pH gradient as described above.

In some embodiments, the methods described herein do not comprise a further purification step to remove a virus filter foulant, and the purified polypeptides have a purity of at least about 98% or about 99% monomer.

In some embodiments, the purification method does not comprise a further purification step to remove a basic or an acidic polypeptide variant.

The purified polypeptide using the methods described herein may be subjected to additional purification steps either prior to, during, or following the Protein A chromatography step. Exemplary further purification steps include, but are not limited to, hydroxylapatite chromatography; dialysis; affinity chromatography using an antibody to capture the protein; hydrophobic interaction chromatography (HIC) (e.g, fractionation on a HIC); ammonium sulphate precipitation; Polyethylene glycol or polyethylene glycol derivative precipitation, anion or cation exchange chromatography; ethanol precipitation; reverse phase HPLC; chromatography on silica; chromatofocusing; SDS-PAGE, virus filtration, gel filtration, and weak partitioning chromatography.

In some embodiments, the polypeptides are further subjected to a virus filtration step. For example, a parvovirus filter can be used in the virus filtration step following the step of Protein A chromatography using a pH gradient as described herein.

In some embodiments, the polypeptides are further subjected to an ion exchange chromatography step. In some embodiments, the ion exchange chromatography step comprises a cation exchange chromatography step. In some embodiments, the ion exchange chromatography step comprises an anion exchange chromatography step. In some embodiments, the ion exchange chromatography step comprises a cation exchange chromatography step and an anion exchange chromatography step.

In some embodiments, the ion exchange chromatography step runs continuously after the Protein A chromatography step as described herein. For example, cation and anion exchange chromatography membranes can be used in place of the standard cation and/or anion exchange chromatography columns following the Protein A chromatography method described herein to achieve purified polypeptides of comparable purity and yield produced by the method of standard Protein A chromatography without the pH gradient followed by standard cation and anion exchange column chromatography steps.

In some embodiments, the methods described herein are manufacturing scale or commercial processes. As used herein, manufacturing scale or commercial processes refers to a large scale purification of protein/polypeptide, for example, at about 1 kL to about 25 kL fermentation scale protein/polypeptide product per purification process.

Polypeptides

The polypeptide or protein to be purified using the methods described herein includes, but is not limited to, antibody, immunoadhesin, or a polypeptide fused to, or conjugated with a $C_H2/C_H3$ region. Techniques for generating such molecules are discussed below.

Antibodies

Antibodies within the scope of the present invention include, but are not limited to: anti-CD20 antibodies such as chimeric anti-CD20 "C2B8" as in U.S. Pat. No. 5,736,137 (RITUXAN®); anti-VEGF antibodies, including humanized and/or affinity matured anti-VEGF antibodies such as the humanized anti-VEGF antibody huA4.6.1 AVASTIN® (Kim et al., Growth Factors, 7:53-64 (1992), International Publication No. WO 96/30046, and WO 98/45331, published Oct. 15, 1998) and V3LA; anti-MUC16 antibody; anti-CD4 antibodies such as the cM-7412 antibody (Choy et al. Arthritis Rheum. 39(1):52-56 (1996)) and the Ibalizumab (TNX355) antibody; anti-MET antibodies such as one-armed 5D5 anti-C-Met antibody; anti-HER2 antibodies Trastuzumab (HERCEPTIN®) (Carter et al., Proc. Natl. Acad. Sci. USA, 89:4285-4289 (1992), U.S. Pat. No. 5,725,856) and humanized 2C4 (WO01/00245, Adams et al.), a chimeric or humanized variant of the 2H7 antibody as in U.S. Pat. No. 5,721,108B1, or Tositumomab (BEXXAR®); anti-IL-8 antibodies (St John et al., Chest, 103:932 (1993), and International Publication No. WO 95/23865); anti-prostate stem cell antigen (PSCA) antibodies (WO01/40309); anti-CD40 antibodies, including S2C6 and humanized variants thereof (WO00/75348); anti-CD1 antibodies (U.S. Pat. No. 5,622,700, WO 98/23761, Steppe et al., Transplant Intl. 4:3-7 (1991), and Hourmant et al., Transplantation 58:377-380 (1994)); anti-CD18 (U.S. Pat. No. 5,622,700, issued Apr. 22, 1997, or as in WO 97/26912, published Jul. 31, 1997); anti-IgE antibodies (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338, Presta et al., J. Immunol. 151:2623-2632 (1993), and International Publication No. WO 95/19181); anti-Apo-2 receptor antibodies (WO 98/51793 published Nov. 19, 1998); anti-TNF-α antibodies, including cA2 (REMICADE®), CDP571 and MAK-195 (See, U.S. Pat. No. 5,672,347 issued Sep. 30, 1997, Lorenz et al. J. Immunol. 156(4):1646-1653(1996), and Dhainaut et al. Crit. Care Med. 23(9):1461-1469 (1995)); anti-Tissue Factor (TF) antibodies (European Patent No. 0 420 937 B1 granted Nov. 9, 1994); anti-human α4β7 integrin antibodies (WO 98/06248 published Feb. 19, 1998); anti-epidermal growth factor receptor (EGFR) antibodies (e.g. chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-Tac antibodies such as CHI-621 (SIMULECT® and ZENAPAX® (See U.S. Pat. No. 5,693,762 issued Dec. 2, 1997); anti-CD52 antibodies such as CAMPATH-1H (Riechmann et al. Nature 332:323-337 (1988)); anti-Fc receptor antibodies such as the M22 antibody directed against Fcγ RI as in Graziano et al. *J. Immunol.* 155(10):4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J Immunol.* 26(1): 1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibodies, such as OvaRex; anti-idiotypic GD3 epitope antibody BEC2; anti-αvB3 antibodies, including VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

Aside from the antibodies specifically identified above, the skilled practitioner can generate antibodies directed against an antigen of interest, e.g., using the techniques described below.

(i) Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22 and CD34; members of the ErbB receptor family such as the EGFR, HER2, HER3 or HER4 receptor; cell adhesion molecules such as LFA-1, Mac1, p1 50,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to {fraction (1/10)} the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al, *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxylapatite chromatography, gel electrophoresis, dialysis, or affinity chromatography. Preferably the Protein A affinity chromatography procedure using a pH gradient described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Monoclonal antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional hybridoma techniques for isolation of monoclonal antibodies.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature* Biotech 14:309 (1996)).

(v) Antibody Fragments

Various techniques have been developed for the production of antibody fragments. Traditionally, these fragments were derived via proteolytic digestion of intact antibodies (see, e.g., Morimoto et al. *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. A single chain Fv fragment (scFv) can also be isolated. See WO 93/16185. Other techniques for the production of antibody fragments will be apparent to the skilled practitioner.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$ and $V_L$) which form a pair of antigen binding regions. Linear antibodies can be bispecific or monospecific.

Antibodies with more than two valencies are contemplated. For example, trispecific antibodies can be prepared. Tutt et al. *J. Immunol* 147: 60 (1991).

Immunoadhesins

The simplest and most straightforward immunoadhesin design combines the binding domain(s) of the adhesin (e.g., the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In some embodiments, the adhesin sequence is fused to the N-terminus of the Fc domain of immunoglobulin $G_1$ (Ig $G_1$). It is possible to fuse the entire heavy chain constant region to the adhesin sequence. However, preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In some embodiments, the adhesin amino acid sequence is fused to (a) the hinge region and or $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagramed below:
(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $(A-Y)_n$-$(V_L C_L$-$V_H C_H)_2$,
wherein each A represents identical or different adhesin amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., *Mol. Immunol.* 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g., Aruffo et al., *Cell* 61:1303-1313 (1990); and Stamenkovic et al., *Cell* 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

Other $C_H2$/$C_H3$ Region-Containing Polypeptides

The polypeptide to be purified is one which is fused to, or conjugated with, a $C_H2$/$C_H3$ region. Such fusion polypeptides may be produced so as to increase the serum half-life of the protein and/or to facilitate purification of the protein by Protein A affinity chromatography. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a ner growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD1 9 and CD20; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as EGFR, HER2, HER3 or HER4 receptor; and fragments of any of the above-listed polypeptides.

Expression of Polypeptides

The polypeptide to be purified using the method described herein is generally produced using recombinant techniques. The polypeptide may also be produced by peptide synthesis (or other synthetic means) or isolated from a native source.

For recombinant production of the polypeptide, the nucleic acid encoding it is isolated and inserted into a replicable vector for further cloning (amplification of the DNA) or for expression. DNA encoding the polypeptide is readily isolated and sequenced using conventional procedures (e.g., where the polypeptide is an antibody by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g., as described in U.S. Pat. No. 5,534,615, specifically incorporated herein by reference).

Suitable host cells for cloning or expressing the DNA in the vectors herein are the prokaryote, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli*, Enterobacter, Erwinia, Klebsiella, Proteus, Salmonella, e.g., *Salmonella typhimurium*, Serratia, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines include, but are not limited to, monkey kidney CV1 cells transformed by SV40 (COS-7, ATCC CRL 1651); human embryonic kidney cells (293 or 293 cells subcloned for growth in suspension culture, Graham et al., J. Gen Virol. 36:59 (1977)); baby hamster kidney cells (BHK, ATCC CCL 10); Chinese hamster ovary cells/DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and human hepatoma cells (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

The host cells used to produce the polypeptide used in the methods of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927, 762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source.

Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

Compositions Including Pharmaceutical Formulations Comprising Polypeptides

The invention also includes compositions, such as pharmaceutical formulations. A pharmaceutical formulation comprising the polypeptide purified by the methods of the present invention, optionally conjugated with a heterologous molecule, may be prepared by mixing the polypeptide having the desired degree of purity with optional pharmaceutically acceptable carriers, excipients or stabilizers (Remington's Pharmaceutical Sciences 21st edition (2005)), in the form of lyophilized formulations or aqueous solutions.

The polypeptide product comprising a $C_H2/C_H3$ region purified by the methods described herein can have the desired degree of purity of at least about 98% monomer or at least about 99% monomer.

"Pharmaceutically acceptable" carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 21st edition (2005).

The formulation to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The polypeptide purified as disclosed herein or the composition comprising the polypeptide and a pharmaceutically acceptable carrier is then used for various diagnostic, therapeutic or other uses known for such polypeptides and compositions. For example, the polypeptide may be used to treat a disorder in a mammal by administering a therapeutically effective amount of the polypeptide to the mammal.

The following examples are provided to illustrate, but not to limit, the invention.

EXAMPLES

It is understood that the examples and embodiments described herein are for illustrative purposes only and that various modifications or changes in light thereof will be suggested to persons skilled in the art and are to be included within the spirit and purview of this application.

Example 1 pH Gradient Elution Protein A Chromatography

Six different proteins containing the $C_H2/C_H3$ regions, anti-VEGF antibody #1, anti-CD20 antibody, anti-VEGF antibody #2, anti-MUC16 antibody, anti-CD4 antibody, and an armed anti-Met antibody were purified using a pH step-gradient elution method on a Protein A chromatography column. The method is outlined in Table 1.

TABLE 1

| Run Phase | Specifics |
| --- | --- |
| Column Equilibration | Tris buffer, pH 7 |
| Protein Load | Prefiltered HCCF, 14-37 g/L |
| Washes | Various buffers |
| pH Step Gradient Elution | pH Gradient: 35-60% B; A: Acetate, pH 5.0/B: Formate, pH 2.7 |
| Column Regeneration | NaOH |
| Column Storage | Benzyl alcohol and acetate storage buffer |

Experimental Procedures

A Unicorn method file was constructed using the protein load and buffer composition/pH parameters as listed in Table 1. This file was executed by a GE Healthcare AKTA (GE Healthcare) Explorer FPLC (Fast Protein Liquid Chromatography) system. FPLC was a bench-scale instrument made of plastic piping and pumps that simulated a manufacturing purification process. FPLC produced a "pH gradient" phase by mixing two buffers in a programmed changing proportion by using a two pump (A pump and B pump) system where the flow rate was maintained and the percent of the flow each of the pumps delivered changed. Designated in the Unicorn program was one "% B" to another over a set volume (number of column volumes).

At the column equilibration phase, the column was taken out of storage solution as listed in Table 1 and prepared for loading the protein materials. At the protein loading phase, HCCF (Harvested Cell Culture Fluid) was prefiltered using a 0.2 micron pore size vacuum filter and was loaded onto the Protein A column (MABSELECT™, MABSELECT SURE™, POROS® MABCAPTURE™ A, PROSEP® Va, or PROSEP® Ultra Plus). Proteins were loaded at a density at the range of 14-37 g/L. Most runs were done at 21 g/L. At the Wash 1 phase, the Wash 1 buffer was used to push any load left in the AKTA lines onto the column. At the Wash 2 phase, impurities such as CHOP (Chinese Hamster Ovary Protein) was removed by the Wash 2 buffer. At the Wash 3 phase, the Wash 3 buffer was used to remove the Wash 2 buffer and the associated impurities from the column to prepare for the elution phase. At the pH step-gradient elution phase, a gradient formed by the precise manipulation of two pH buffers of different pHs by a two pump system was used to gradually move from one pH mix of the two buffers to another mix, set by percents. The elution parameter of "35-60% B" correlates to a pH gradient range of about 4.3-3.7. More specifically, 35% B corresponds to elution buffer pH of 4.34, buffer composition of 16.25 mM acetate, 8.75 mM formate, and buffer conductivity of 1039 uS/cm. 60% B corresponds to elution buffer pH of 3.69, buffer composition of 10 mM acetate and 15 mM formate, and buffer conductivity of 763 uS/cm. During this elution phase of most runs, fractions were taken throughout the elution and assayed using a size exclusion HPLC assay to determine monomer versus size variant (HMWS (High Molecular Weight Species), dimer, or fragment) elution behaviors. These fractions were also submitted to a CHOP assay for selected run, and all fractions were measured for protein concentration using a NanoDrop UV spectrophotometer (Thermo Fischer Scientific, Wilmington, Del.). At the regeneration phase, regeneration buffer was used to wash off any tightly bound impurities or leftover product to minimize carryover between runs. At the storage phase, the Protein A column was removed of regeneration buffer and stored in a solution that was designed to maintain column integrity over time in disuse.

Phase lengths and flow rates were measured in CVs and centimeters per hour, respectively. Flow rate was scaled by centimeters per hour (divide the flow rate in cm/hr by the bed height of the column in cm to arrive column volumes per hour, also a standard unit) due to pressure concerns.

Chromatograms were collected and analyzed by the AKTA (GE Healthcare) FPLC purification system and its associated Unicorn software package. After the column A purification run was performed, traces of the UV absorbance, pH, and conductivity (as well as other measured values or program instructions/logbooks) were accessed and examined.

a. Size Exclusion Chromatography (SEC) Assay

An analytical size exclusion chromatography (SEC) assay was run on an Agilent 1200 series HPLC (Agilent Technologies, USA, part G1329A) and used to determine the relative levels of high molecular weight species (HMWS), dimer, monomer, and fragment for collected samples. A 14.24 mL TSK G3000SWXL, 7.8 mmD×300 mmH (Tosoh Bioscience, Tokyo, Japan, part 08541) column was used. Each sample was either diluted to approximately 0.5 g/L antibody using the potassium phosphate/potassium chloride HPLC running buffer or sample injections were modified to standardize mass loaded to the assay column. All samples were prepared in Agilent HPLC 1.5 mL glass vials. Runs were 30 minutes with a 0.5 mL/min flow rate. Sample injections were adjusted so that approximately 25 ng of antibody was loaded per sample. Blanks containing the samples' respective background buffers were run with each sample set. UV 280 nm absorbance curves were analyzed either manually using ChemStation (Agilent Technologies) or automatically using CHROMELEON® (DIONEX, Sunnyvale, Calif.) software to integrate peaks separately to obtain percentage values of species for the samples. Percent values obtained from this assay can be multiplied by the concentration (mg/mL) of the fraction to get an actual concentrations or masses for each size variant species in the sample (e.g., SEC result: 4% HMWS, 3% dimer, 92% monomer, 1% fragment; sample concentration: 2 g/L; sample volume: 10 mL; 1.84 g/L monomer, 18.4 mg monomer total in sample).

b. CHOP assay

Samples from selected runs were submitted to an assay group that performed a standard and validated enzyme linked immunosorbent assay (ELISA) to quantitate the levels of CHOP. Affinity-purified goat anti-CHOP antibodies were immobilized on microtiter plate wells. Dilutions of the samples containing CHOP, standards, and controls, were incubated in the wells, followed by incubation with goat anti-CHOP antibodies conjugated to horseradish peroxidase. The horseradish peroxidase enzymatic activity was detected with o-phenylenediamine dihydrochloride. The CHOP was quantitated by reading absorbance at 492 nm in a microtiter plate reader. A computer curve-fitting program was used to generate the standard curve and automatically calculate the sample concentration. The assay range for the ELISA was typically 5 ng/ml to 320 ng/ml. Results were standardized to ppm for pool comparisons.

Results

The elution shape of a step-gradient is shown in FIG. 1. All proteins were eluted by the end of the pH decline. A larger portion of the proteins were eluted from the column more rapidly, but enough proteins remained on the column and were eluted during the gradient. At lower pH, the separation between the desired product (elution range of around pH 4.6 to 3.7 with slight molecule to molecule variation) and undesirable aggregate (elution range around pH 3.9 to 3.5) occurred.

In all six protein molecules tested (anti-VEGF antibody #1, anti-CD20 antibody, anti-VEGF antibody #2, anti-MUC16 antibody, anti-CD4 antibody, and one-armed anti-Met antibody), high percentages (~100%) of monomer were observed in the initial gradient fractions and the tail end portion of the gradient contained much higher levels of aggregated species (>50%). These SEC results are shown in FIGS. 2-4B. Since this set of tested molecules encompasses larger classes of protein molecules (e.g., chimeric antibodies, thioMabs (recombinant monoclonal antibodies having a point mutation by replacing one amino acid residue with cysteine), IgG4s, and antibody fragments produced by *E. coli*), this pH step-gradient method suggest broad applicability to all $C_H2/C_H3$ region-containing polypeptides/proteins (e.g., Fc region).

Example 2

Figure 5:
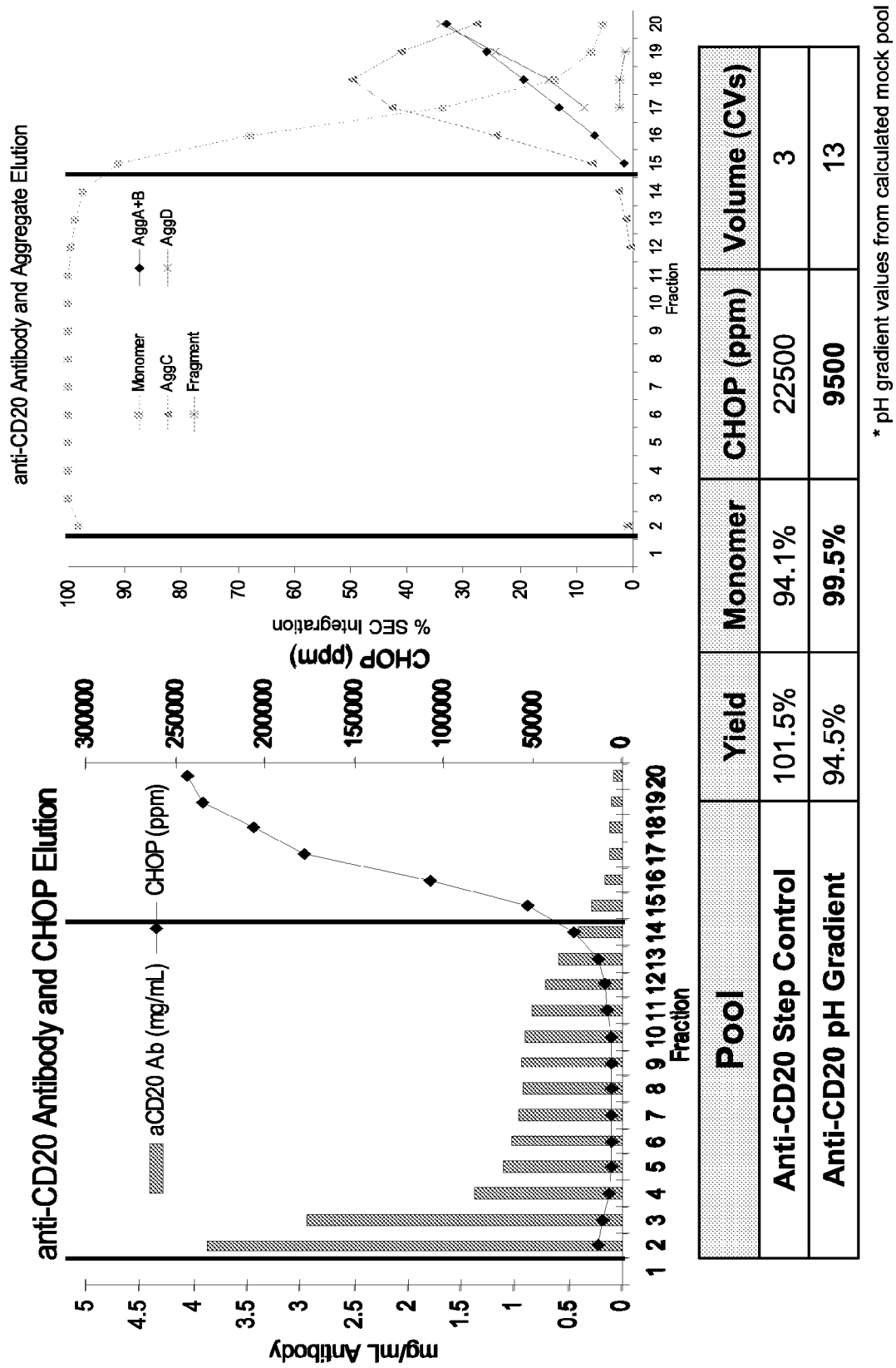
FIG. 5 shows a side-by-side comparison between an anti-CD20 antibody standard step elution (control; eluting proteins at pH at or below 3.6 without the pH gradient) and pH step-gradient elution. The anti-CD20 antibody and CHOP elution graph on the left panel shows the CHOP levels per fraction in ppm (parts per million; unit used for standardizing measurement of impurities to amount of product). The anti-CD20 antibody and aggregate elution graph on the right panel shows the SEC peak integration values per fraction through the gradient elution. The vertical lines in both the left and right panels represent the mock pooling of the contained fractions that would generate a pH gradient elution pool with the characteristics shown in the table at the bottom of the slide.

CHOP Separation for Anti-CD20 Antibody, Anti-VEGF Antibody #1, and Anti-MUC16 Antibody over a Protein A Chromatography Column Using a Standard Step Elution and a pH Step-Gradient Elution Using the method of pH step-gradient elution protein as described in Example 1, the anti-CD20 antibody levels per fraction in mg/mL (from the bench top offline UV 280 absorbance, which tracked with the online AKTA/Unicorn UV 280 readings for the step-gradient elution phase as seen on the anti-VEGF antibody #1 chromatogram in FIG. 1A) and the CHOP levels per fraction in ppm were measured. As seen in the left panel of FIG. 5 (anti-CD20 antibody and CHOP elution), the later fractions at lower pH of the pH step-gradient elution contained very little anti-CD20 antibody compared to the amount of CHOP. Data from the control run done at the same time as the anti-CD20 antibody step-gradient pH elution is shown in the top row of the table in FIG. 5. Control run was using the same conditions as described in Table 1, except that no pH step-gradient was used during the protein elution phase, and the protein was eluted at or below pH 3.6. The bottom row shows a small, but acceptable, decrease in the anti-CD20 antibody yield using the pH step-gradient. (note: this yield loss due to aggregate removal is expected; yield is calculated using the HCCF titer value that includes aggregates in the total amount of product loaded on the column). About 5% less aggregate and half of the CHOP levels were observed in comparison to the control pool. The results establish an unexpected benefit of increased purity using the pH step-gradient elution.

Figure 6:
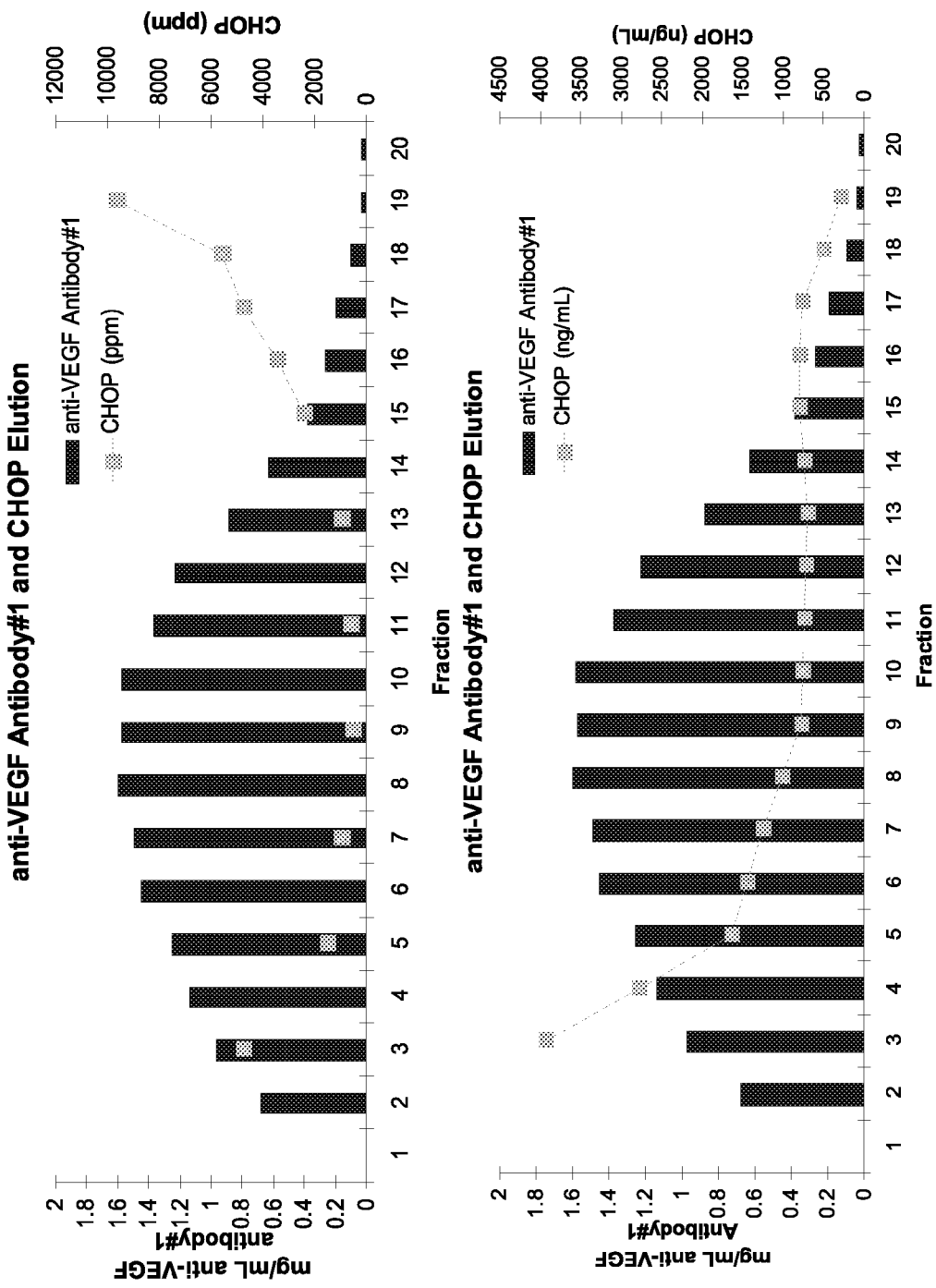
FIG. 6 shows the CHOP separation for an anti-VEGF antibody #1. The CHOP levels per fraction are expressed in ppm or ng/mL.

CHOP separations for both anti-VEGF antibody #1 and anti-MUC16 antibody were also performed using the pH step-gradient method described in Example 1. Similar to the pattern observed in anti-CD20 antibody CHOP graph, more CHOP was eluted at the end of the pH gradient in proportion to the elution of anti-VEGF antibody, indicating that the pH step-gradient elution separated host cell impurities for this protein molecule as well as the anti-CD20 antibody. See FIG. 6. For CHOP separation in the anti-MUC16 antibody, this antibody had much higher CHOP levels in comparison to the elution pattern observed in anti-VEGF antibody#1. See FIG. 7. Accordingly, a significant amount of CHOP can be fractionated from anti-MUC16 antibody by using the pH step-gradient method as described above.

Example 3

Virus Particle Clearance Using pH Gradient Elution Protein A Chromatography

Using the method of pH step-gradient elution protein A chromatography as described in Example 1, the virus particle clearance of anti-VEGF antibody #1 was measured.
Step-Gradient pH Elution Protein A Chromatography
All phases and buffers were the same as those used in Example 1. Fractions were tested for retrovirus-like particle counts using a quantitative polymerase chain reaction assay.
a. Retrovirus-Like Particle Quantitative Polymerase Chain Reaction (RVLP QPCR) Assay
The RVLP endogenous virus particle assay is a real-time quantitative PCR assay. Viral RNA was extracted from samples using Qiagen EZ1 (Qiagen, Valencia, Calif.). Sample sizes were 0.4 mL (undiluted and 1:10 diluted HCCF, undiluted protein A pool). Extraction efficiency was confirmed by including a reference standard HCCF sample with a known CHO retrovirus particle titer. Genomic DNA was removed by DNase digestions by treating the extraction eluate with 0.2 units/mL of DNase I at an elevated temperature for 30 min. The DNase was then heat inactivated at 70° C. for 15 min. The absence of retroviral DNA was confirmed by assaying the samples without reverse transcriptase.

Figure 18:
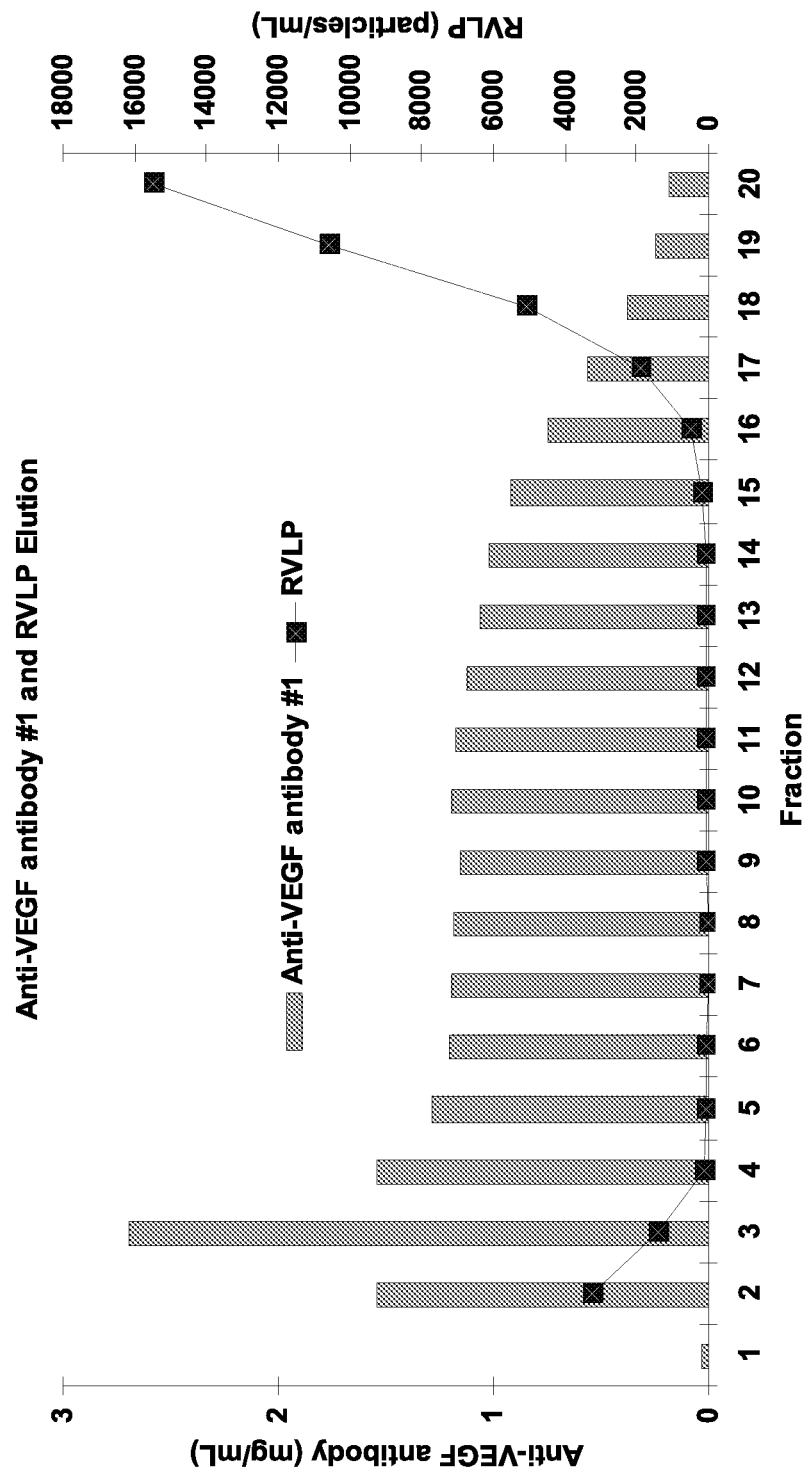
FIG. 18 is RVLP (Retrovirus-like Particle) particle counts from QPCR (Quantitative Polymerase Chain Reaction) analysis per fraction graphed against anti-VEGF antibody #1 product elution. The majority of the RVLPs eluted late in the gradient where little product elution occurred.
Figure 19:
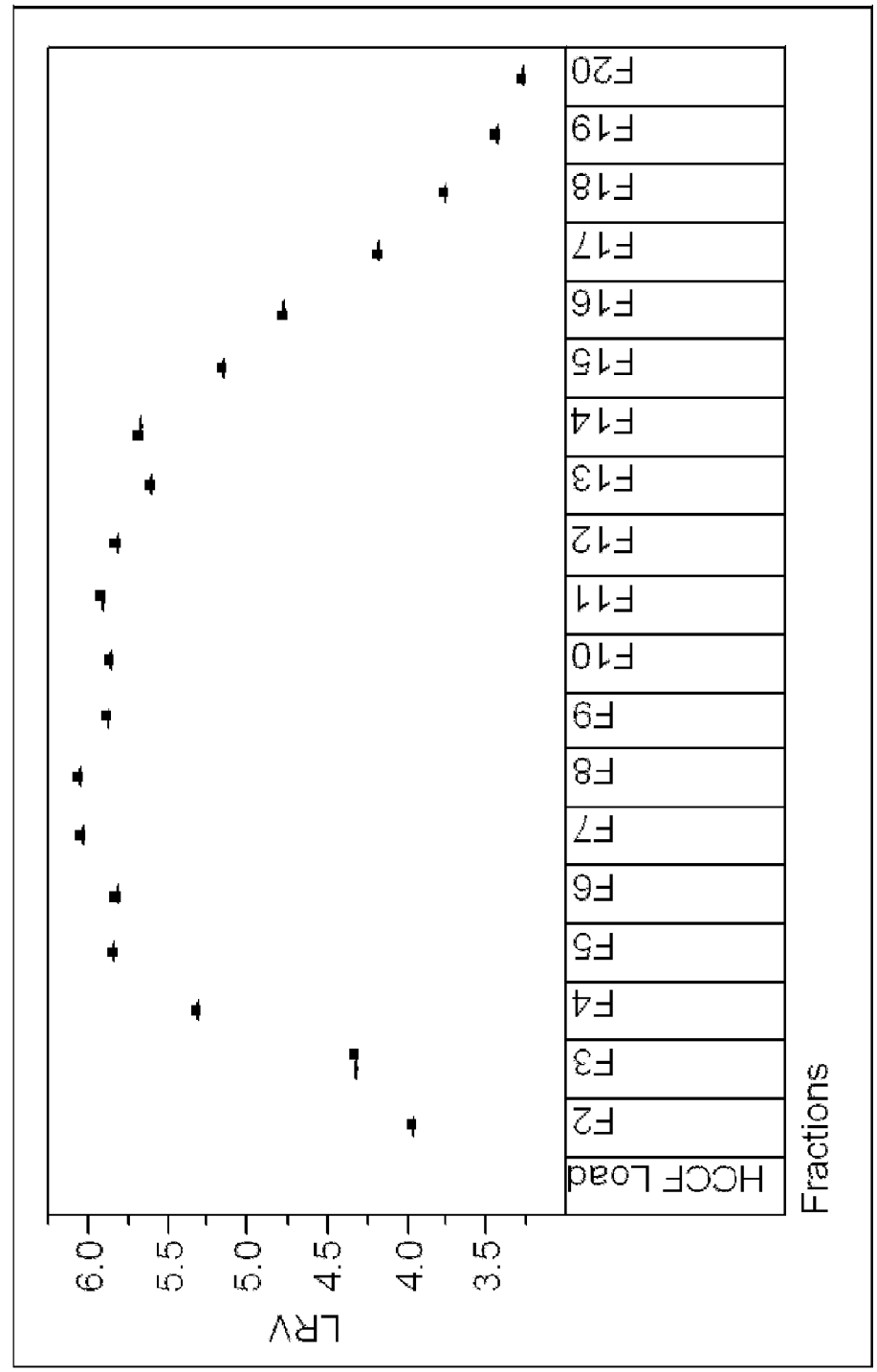
FIG. 19 is LRV (log 10 reduction of virus) for each fraction in the Protein A pH step-gradient elution of anti-VEGF antibody #1.
Figure 20:
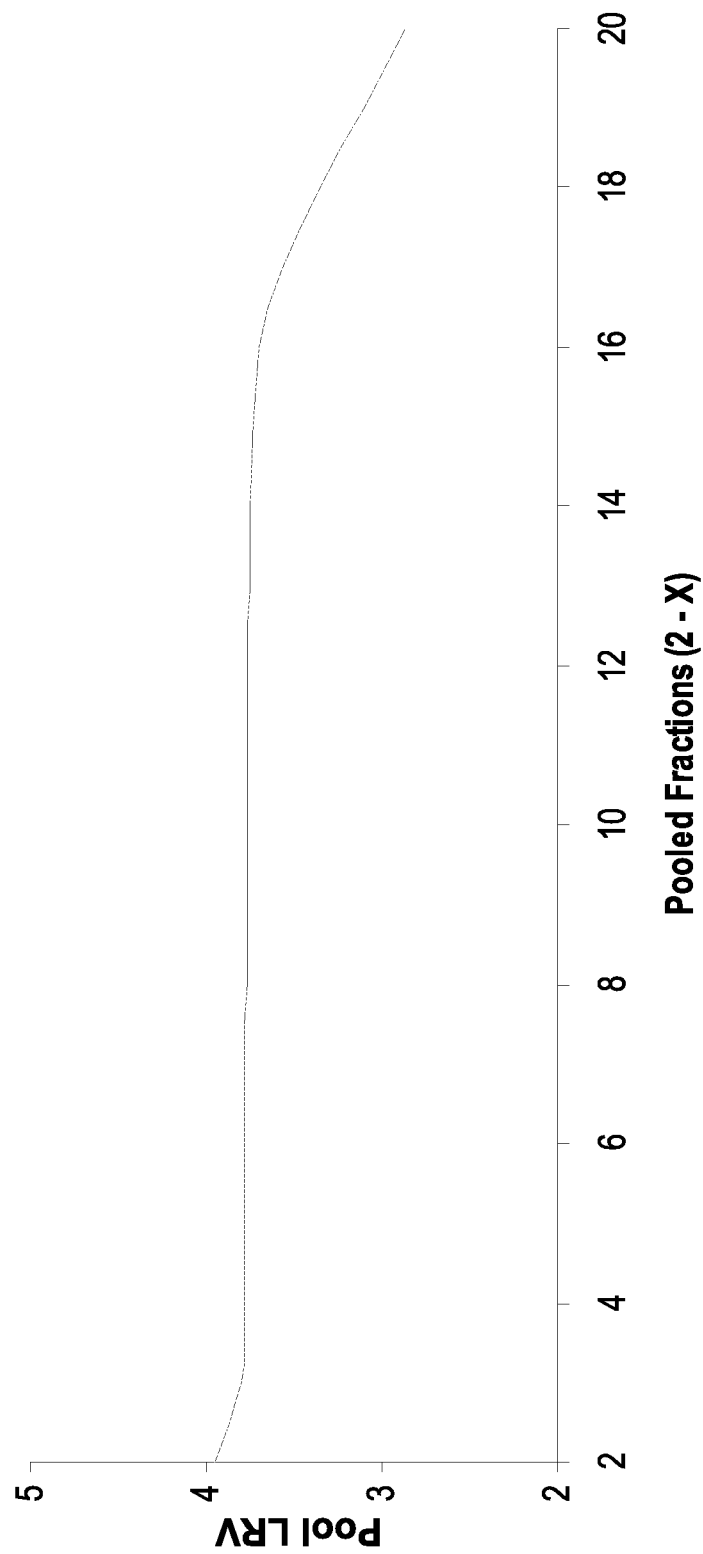
FIG. 20 shows cumulative LRVs for mock pools of the fraction, showing that higher LRVs can be achieved in the Protein A pool if later fractions are omitted.

Real-time quantitative PCR assays to measure CHO retrovirus genomes were performed as described in De Wit et al. (Biologicals, 28(3):137-48 (2000)), but with the use of a new probe at nearby region. The reagents and procedures were also updated and improved. Primers and probe sequences were designed to amplify a fragment in the highly conserved pol region from the CHO type C retrovirus genome. Each retrovirus-like particle contains two genomic RNA molecules. Oligonucleotide probes and primers were ordered from Applied Biosystems (Foster City, Calif.) and Invitrogen (Carlsbad, Calif.). Viral clearance was expressed as log 10 reduction value, or LRV, which is the difference of log 10 (total virus) in the protein (HCCF) load and in the product pool. Total virus was obtained from virus titers (particles/ml or nU/mL) in samples and sample volume (mL) FIG. 18 shows the endogenous virus-like particle count for each fraction taken from the pH step-gradient elution. Some virus eluted at the start of the gradient in the large peak, but a larger portion of the virus eluted at the tail end of the elution. Accordingly, separation of these RVLPs from product can benefit pH step-gradient or full-gradient elution Protein A chromatography overall efficiency in terms of viral clearance. FIG. 19 shows LRV for each fraction in comparison to the HCCF load. The graph was based on a calculation using the values from FIG. 18. A large decrease in the LRV was observed in the later aggregate rich elution fractions. LRV was high (desirable effect) in the middle eluting, higher polypeptide monomer fractions.

Example 4

Figure 17:
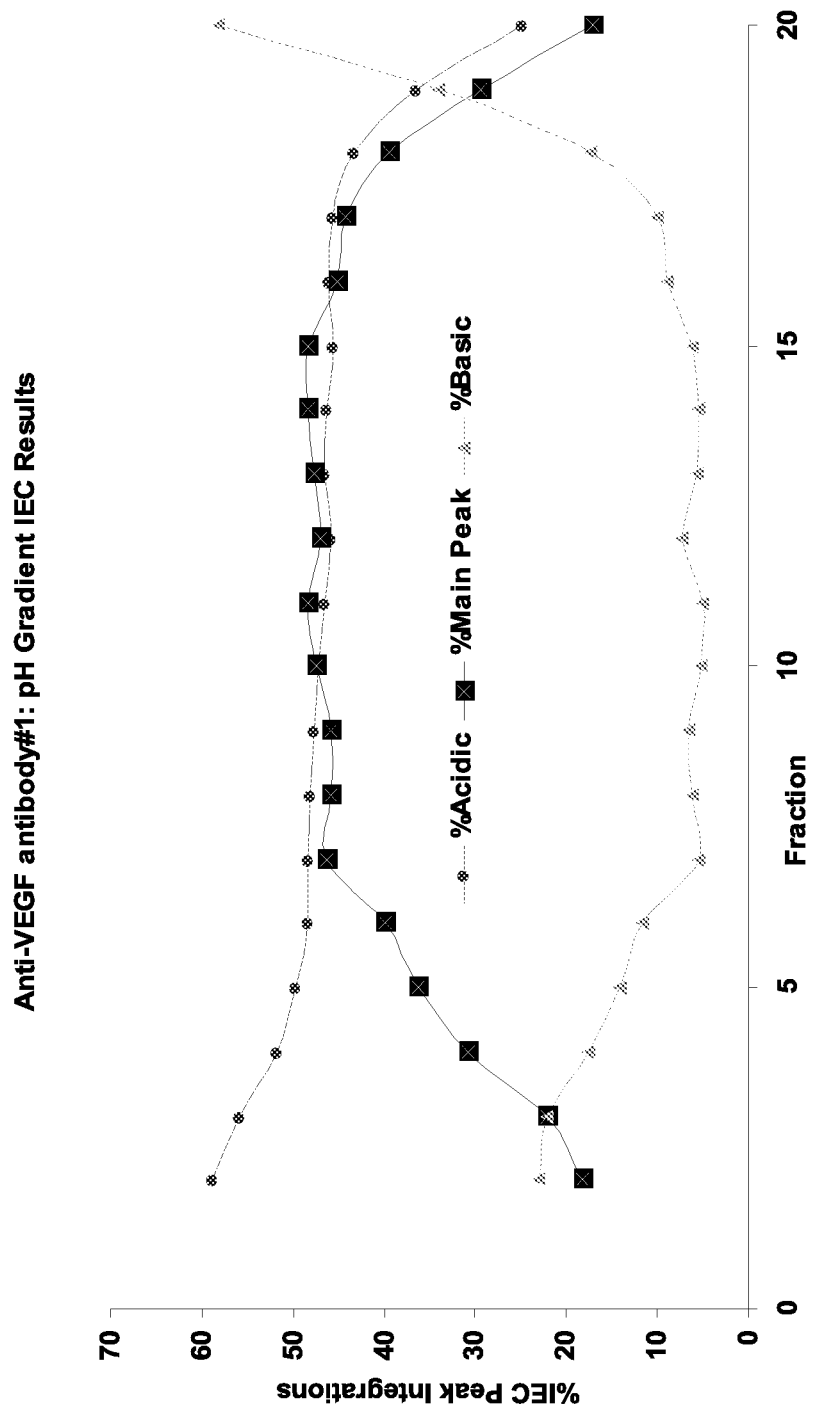
FIG. 17 is an ion exchange variant assay peak integration across Protein A pH step-gradient elution fractions, indicating the separation of basic polypeptide variant in the tail portion of the step-gradient elution.

Basic Polypeptide Variants Clearance Using pH Gradient Elution Protein A Chromatography Using the method of pH step-gradient elution protein A chromatography as described in Example 1, the basic polypeptide variants (or basic variants) clearance of anti-VEGF antibody #1 was measured.
Step-Gradient pH Elution Protein A Chromatography
All phases and buffers were the same as those used in Example 1. Fractions were submitted to the ion-exchange variant assay.
a. Ion-Exchange Variant Assay
An analytical ion exchange chromatography (IEC) assay was run on an Agilent 1200 series HPLC (Agilent Technologies, USA, part G1329A) and used to determine the relative levels of main peak to acidic and basic charged variants for collected Anti-VEGF antibody #1 samples. A Dionex ProPac WCX-10, 4.6×250 mm (Dionex product no. 054993) column was used with a gradient of ACES [N-(2-Acetamido)-2-aminoethanesulfonic acid] and NaCl under conditions of elevated temperature. Sample preparation included buffer exchanging samples into IEC mobile phase prior to a 20 minute heated digestion with Carboxypeptidase (CpB). Approximately 50 µg of Anti-VEGF antibody #1 was injected into the column per sample. UV 280 nm traces were obtained and integrated using ChemStation (Agilent Technologies) software. Integration percents for each category of acidic, basic, and main peak species were analyzed for ion-exchange variant composition trends across the gradient. FIG. 17 shows the result of the ion exchange variant assay peak integration across 20 Protein A pH step gradient elution fractions. The percent of basic variants present in the fractions increases dramatically in the tail portion of the Protein A pH step-gradient elution. This tail portion of the gradient elution is the same portion where the increased CHOP and aggregation separation were observed, as described in Examples 1 and 2.

Example 5 pH Step-Gradient Elution Using Multiple Protein A Chromatography Columns

Figure 8:
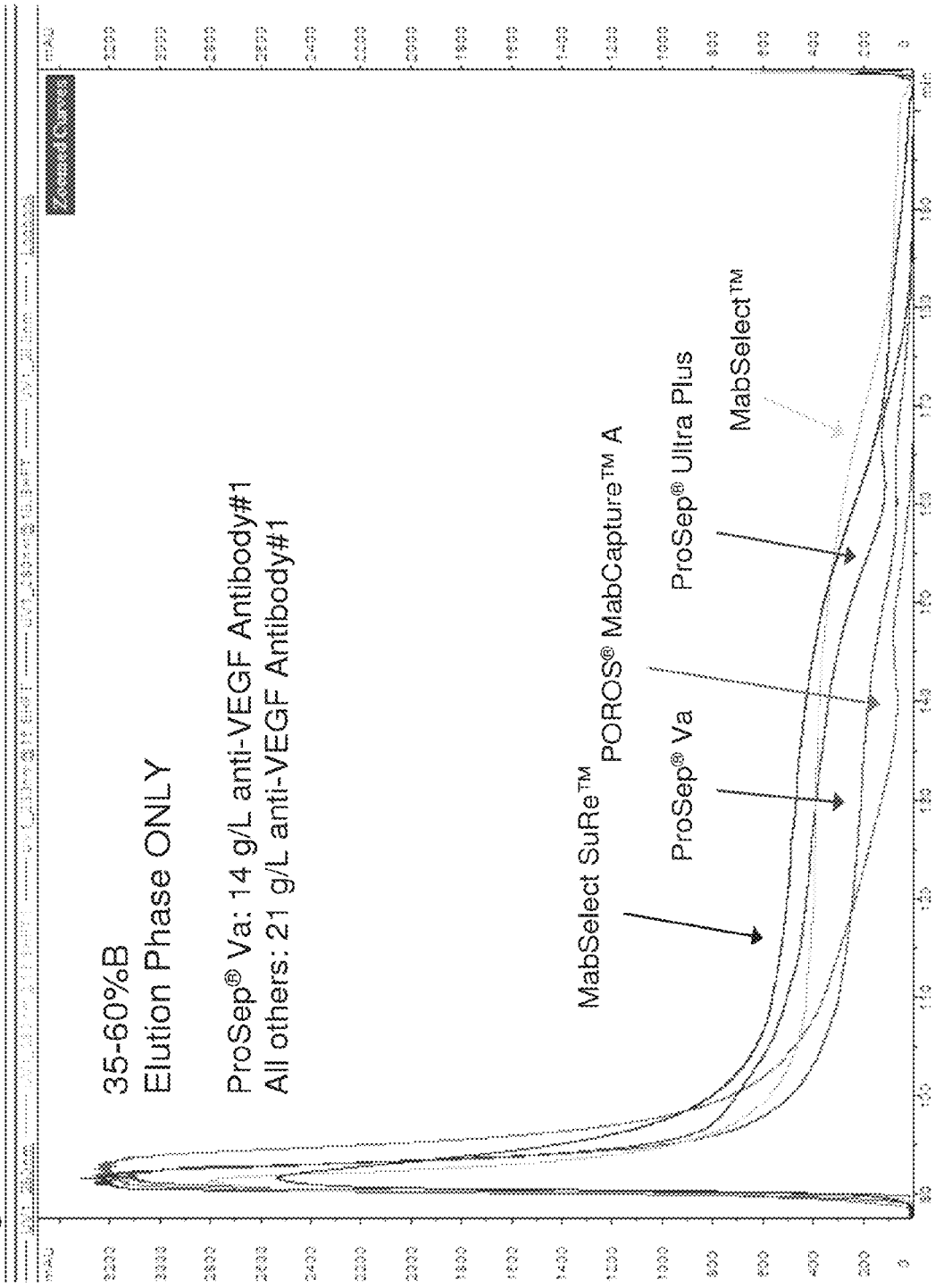
FIG. 8 is a MABSELECT™, MABSELECT SURE™, PROSEP® Va, PROSEP® Ultra Plus, and POROS® MABCAPTURE™ A Protein A resin chromatogram overlay.

Both the MABSELECT SURE™ and the MABSELECT™ resins were tested for the pH step-gradient elution method as described above. These two Protein A resins, although similar in name, have different affinity ligands attached. The MABSELECT™ bears the native Protein A ligand, which bind to the Fc portions of antibodies. The MABSELECT SURE™ bears a modified form of Protein A that has been chemically altered to be stable in solutions of high pH for short amounts of time. The overlayed AKTA elution profiles show that the elution traces are extremely similar for the two Protein A resins. As can be seen by the SEC integration profile for MabSelect in FIG. 8, comparable aggregate separation was achieved using this resin. Other resins tested successfully for aggregate separation were PROSEP® Va, PROSEP® Ultra Plus, and POROS® MAB-CAPTURE™ A. Accordingly, various affinity resins (e.g., MABSELECT™, MABSELECT SUERE™, PROSEP® Va, PROSEP® Ultra Plus, and POROS® MABCAPTURE™) can be used in the pH step-gradient elution method to fractionate impurities.

Example 6

Design of Experiments (DOE) Using Various Parameters for the pH Gradient Elution Method Various parameters that are important in most chromatography processes were explored for anti-VEGF antibody #1 using a 35-run statistically designed study within the ranges shown in Table 2. The "elution start % B" parameter affects the starting pH of the elution phase (which plays a major role in determining the shape of the elution curve. The higher the starting % B, the lower the starting elution pH, the more protein eluted from the column in the first fractions), as well as the slope of the overall gradient. Parameters were varied simultaneously in a fractional factorial study designed to elucidate the main effects as well as the interactions. All runs were fractionated during the elution, and aggregate and concentration were assayed for all fractions. An interpolative calculation was used to determine the mock pool monomer levels for pools that would result in exactly 85% yield (the lower limit of the step yield target) and these values were used to compare the effectiveness of each set of run parameters in separating monomer from aggregate efficiently.

TABLE 2

| DOE Parameter Ranges | | | |
|---|---|---|---|
| Parameter | Low | Target | High |
| Load Density | 19 | 28 | 37 |
| Bed Height | 14 cm | 22 cm | 30 cm |

TABLE 2-continued

| DOE Parameter Ranges | | | |
|---|---|---|---|
| Parameter | Low | Target | High |
| Elution Flow Rate | 140 cm/hr | 210 cm/hr | 350 cm/hr |
| Elution Length | 15 CV | 20 CV | 25 CV |
| Elution Start % B (pH)* | 25 (4.6) | 35 (4.3) | 45 (4.2) |

*All elutions ended at 60% B (pH 3.7)

Experimental Procedures

All parameter changes aside from the column bed height (which requires packing of multiple columns) were examined using the Unicorn software. CV fractions were taken throughout all of the elutions, assayed using the HPLC SEC (as described above), and measured for the protein concentration (UV 280 absorbance as measured on a NanoDrop UV spectrophotometer). In order to best standardize the results for comparison, data from various sets of fractions were compiled and a calculation was used to interpolate the overall yield and SEC profile of a pool from each of the run.

Figure 11:
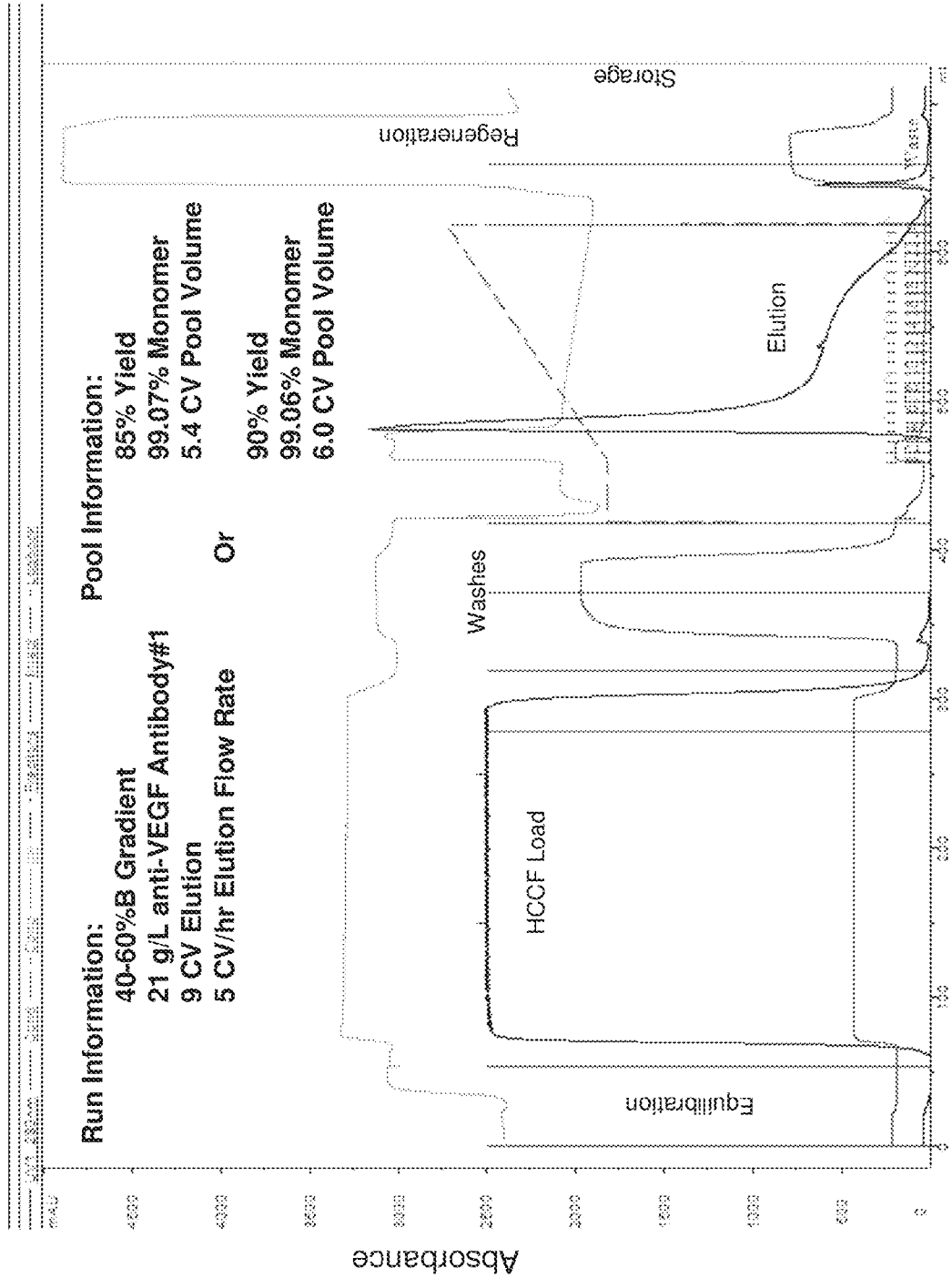
FIG. 11 is an exemplary manufacturing run for the pH step-gradient elution.

The JMP® (SAS, Cary, N.C.) software package was employed to generate a fractional factorial parameter exploration run plan. One of the runs was selected as the "exemplary manufacturing run" from the set because of its high yield, high monomer level, and low pool size (FIG. 11).

Results

Figure 9:
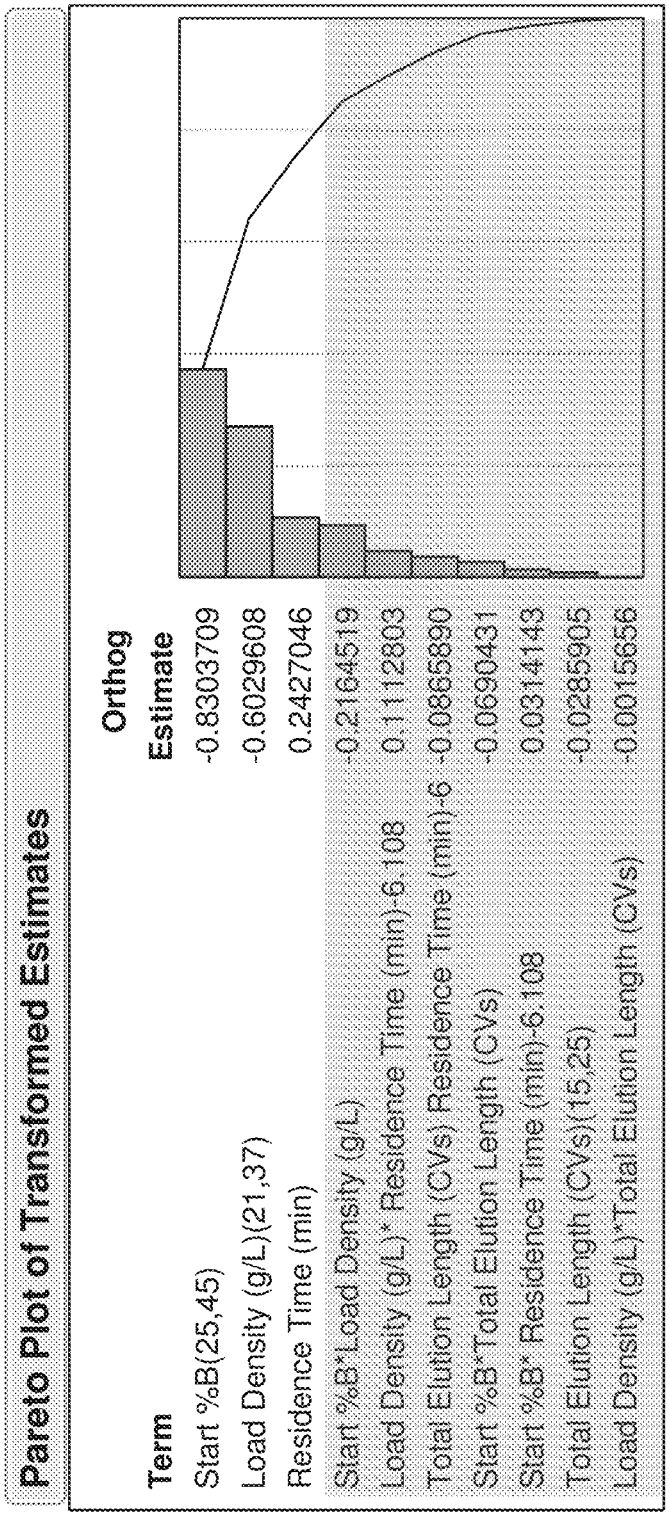
FIG. 9 is a Pareto Plot showing that Start % B (the starting pH and the slope of the elution gradient) is the most influential parameter in determining aggregate separation efficiency, followed by load density and residence time.
Figure 10:
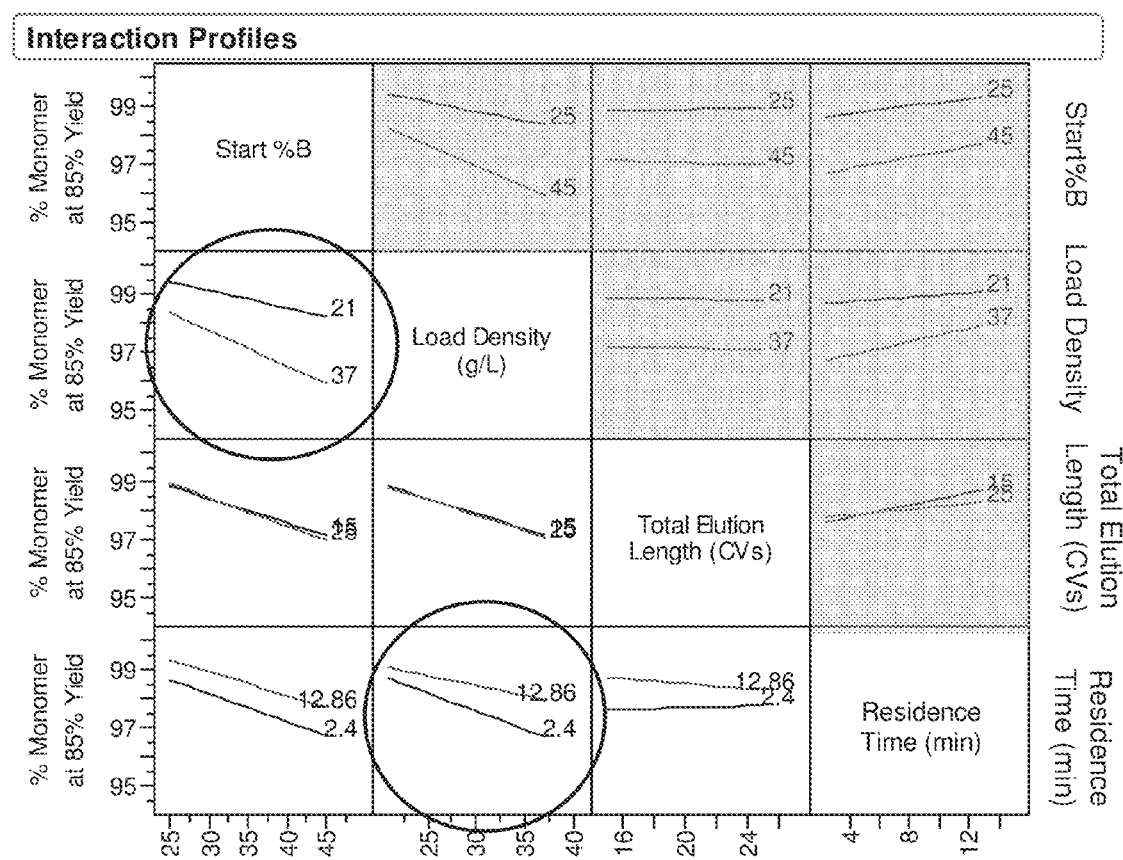
FIG. 10 is an interaction profile for parameters of start % B, load density and start % B, total elution length, and residence time.

Pareto plot of DOE results show that the "Start % B" is the most influential parameter in determining aggregate separation, followed by load density (lower is better) and residence time (residence time was calculated by dividing the controlled parameters of bed height (cm/CV) by flow rate (cm/hr) for hr/CV. Accordingly, the lower the start % B, the higher the elution start pH, and the more efficient the aggregate separation; the lower the load density, the more efficient the aggregate separation; and the higher the residence time, the more efficient the aggregate separation. See FIG. 9. Further, interaction profiles from this study shows that there was an interaction between the parameters of load density and start % B as well as an interaction between the residence time and load density. At increased load densities, the start % B had a greater effect on the monomer levels of 85% yield mock pools than if the run was done at lower load densities. Further, at increased load density, the residence time played a much larger role in the ability of the gradient to fractionate aggregates more efficiently. A lower rate must be used during the elution to achieve high product throughput with the pH step-gradient method. See FIG. 10. FIG. 11 shows that the pool from this run was under 10 CVs (e.g., 5.4 CV or 6 CV) while delivering less than 1% aggregate with greater than 85% yield.

In addition to the main effects (Pareto plot in FIG. 9), interactions (FIG. 10), and exemplary manufacturing run (FIG. 11), it was observed that overall elution length had no effect on aggregate separation, but could be manipulated to decrease the pool size to result in a pool that still has high purity and high yield, but in a lesser volume (which is preferable for manufacturing scale). Also, the use of the pH step-gradient resulted in lower pool volumes with purity nearly comparable to that given by the full gradient (see Example 8). The pH step-gradient was also found to be robust in several process changes, including smaller changes in load density and flow rate, as well as being completely unaffected by bed height.

Example 7

Protein Purification Using Ion Exchange Membrane Chromatography Following the pH Step-Gradient Protein A Chromatography To determine whether downstream column chromatographies could be eliminated from the purification process or substituted with membranes, bench scale cycling of the Protein A pH step-gradient on anti-VEGF antibody #1 (with a pool of less than 1% aggregate and a high yield) was loaded onto downstream charged membranes. MUSTANG® S (Pall corporation) and MUSTANG® Q (Pall corporation) membranes represent a cation exchange membrane and an anion exchange membrane, respectively. Success was measured by the ability of the membranes to achieve the same overall purities and yields as compared to the typical downstream column process.

Experimental Procedures

Parameters used for determining optimal load conditioning for CHOP and aggregate clearance over S and/or Q membranes were taken from prior studies on optimal load conditioning for CHOP clearance over S and/or Q membrane using a Protein A standard step pool in Tables 3A and 3B. In these prior studies, promising results were shown when a Protein A standard step pool was used (control group, using no pH gradient and eluting protein at or below pH 3.6); however, this process had slightly higher CHOP levels than desired and did not clear any aggregates from the process. In these prior studies, membranes had been loaded to 5 kg/L membrane and optimal loading conditions had been found for impurity removal. These same conditions were used for the Protein A step-gradient elution pool to compare the performance of the different Protein A pools on these membranes with the primary impurities targeted as CHOP and aggregate.

TABLE 3A

Prior parameters for determination of optimal load conditioning for CHOP clearance over S or Q membranes

| | |
|---|---|
| Filter | MUSTANG ® S or Q ACRODISC ® |
| Filter Size | 0.18 mL |
| Load | anti-VEGF antibody #1 Protein A Step Pool |
| Load Density | 5 kg/L membrane |
| Flow Rate | 4 mL/min (1333 mV/hr, 112 cm/hr) |
| Assay | CHOP ELISA |

TABLE 3B

Prior parameters for determining whether orthogonal impurity clearance can be achieved by running S and Q membranes in series.

| | |
|---|---|
| Best MUSTANG ® S pool (Protein A Step Pool as load) | load at pH: 5-6, 3 mS/cm; 140 ppm CHOP |
| Best MUSTANG ® Q pool (Protein A Step Pool as load) | load at pH: 8-9, <4 mS/cm; 30 ppm CHOP |
| Best MUSTANG ® Q pool (Best MUSTANG S Pool as load) | load at pH: 8-9, 2.5 mS/cm; 15-20 ppm CHOP |

In the initial studies, Protein A standard step elution pools were conditioned to specific pHs and conductivities and passed through laboratory scale cation (MUSTANG® S) and anion (MUSTANG® Q) exchange membrane units that were connected to the AKTA™ FPLC purification system. Flow rates were maintained and pressure traces were examined for evidence of fouling/permeability decay. Fractions were taken at various load densities and assayed for CHOP (ELISA) and antibody concentrations (UV 280 absorbance on the NanoDrop UV spectrophotometer). The results of these assays were compared at various load densities to find the optimal loading conditions for end CHOP clearance. In the later studies, the Protein A pH step-gradient elution pool was conditioned to the optima found in the initial studies. From this, the performance of the step-gradient elution pool was compared to that of the standard Protein A step elution in ability of the downstream membranes to clear CHOP and other impurities while maintaining high yield and low aggregate levels. Two sizes of cation exchange membrane and three sizes of anion exchange membrane were also used to test reproducibility and scalability of results.

Results

When the Protein A step pool was used as the load for a cation to anion exchange membrane purification series, the lowest CHOP levels obtained were 15-20 ppm for membranes loaded to 5 kg/L membrane. Since the membranes did not clear aggregate, levels of this impurity were unacceptably high in the end pools. In contrast, when the Protein A pH step-gradient elution pool was loaded onto these same membranes, CHOP levels were 0-15 ppm and aggregate levels were still low in the end pools, showing a benefit to the overall process.

Figure 12:
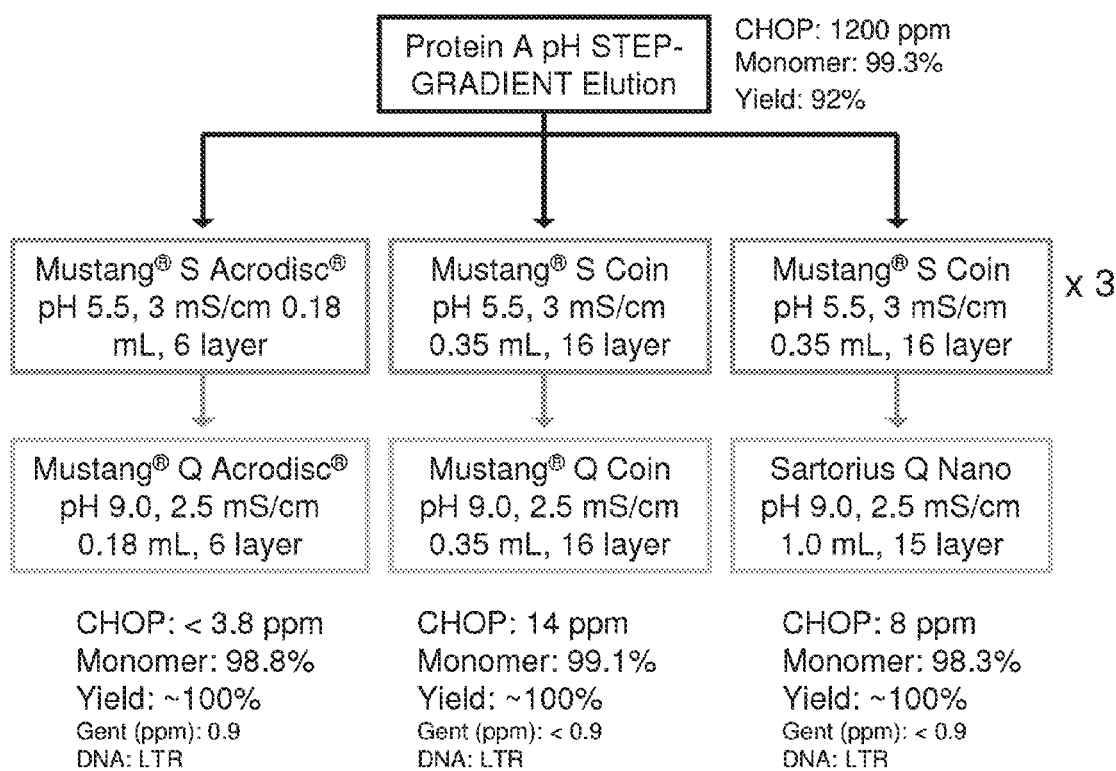
FIG. 12 shows the results of downstream ion exchange membrane study using two sizes of cation exchange membrane and three sizes of anion exchange membrane. The coin and nano units are both representative of manufacturing in the number of membrane layers, while the ACRODISC® units have a reduced number of layers, but are the typical bench scale models used.

Further, end pools of each of the three combinations of ion exchange membranes tested resulted in high yield and high purity end pools. In all cases, the aggregate levels remained low through pH adjustment and membrane processing, and CHOP levels were also lower than what was seen in the prior control studies, showing an unexpected CHOP reduction benefit to using a lower aggregate protein A pool as a feed. See FIG. 12. Accordingly, the use of ion exchange chromatography membranes in place of the usual ion exchange chromatography columns eliminates the need for many typical column chromatography buffers and other time/manufacturing space consuming inconveniences. More importantly, since these charged membranes were used in overload mode (i.e., the load is passed through the membrane to a high loading density with no washing or elution steps needed to generate a highly purified pool), the membranes allow for a continuous purification process downstream of the pH gradient Protein A chromatography step.

Figure 13:
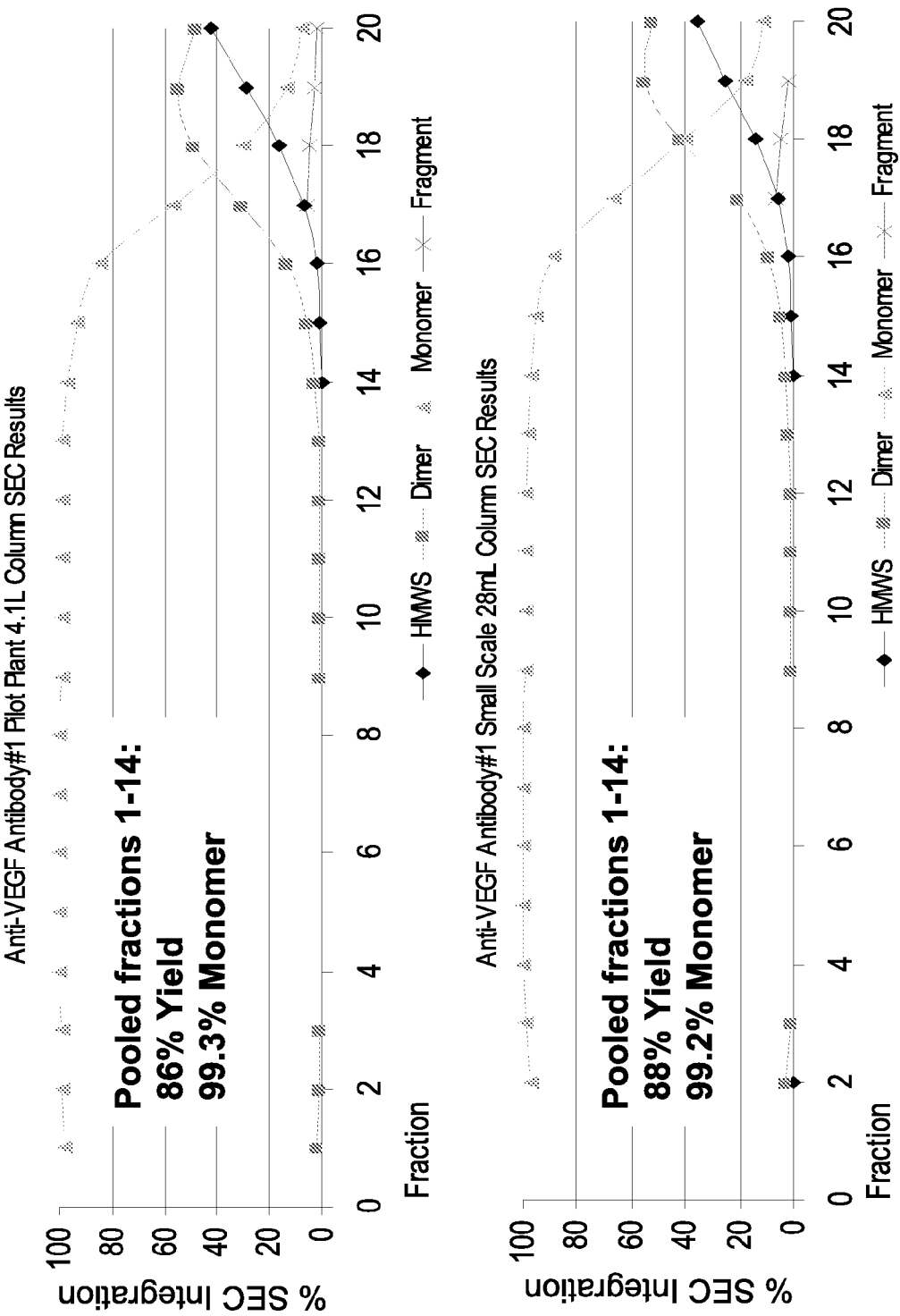
FIG. 13 shows the SEC integration result comparison between a 4.1 L column (Pilot scale) and a 28 mL bench scale column run.

The SEC integration profiles between the pilot scale (4.1 L) and the 28 mL bench scale are also shown to be extremely similar, indicating that Protein A pH step-gradient can be scaled successfully and that any small scale results can be considered indicative of larger scale performance. See FIG. 13. These results indicate an unexpected benefit of reproducibility and scalability of pH step-gradient elution Protein A chromatography.

Example 8

VIRESOLVE® Pro Parvovirus Filter Runs

A. VIRESOLVE® Pro Permeability Decay Comparison

Figure 14:
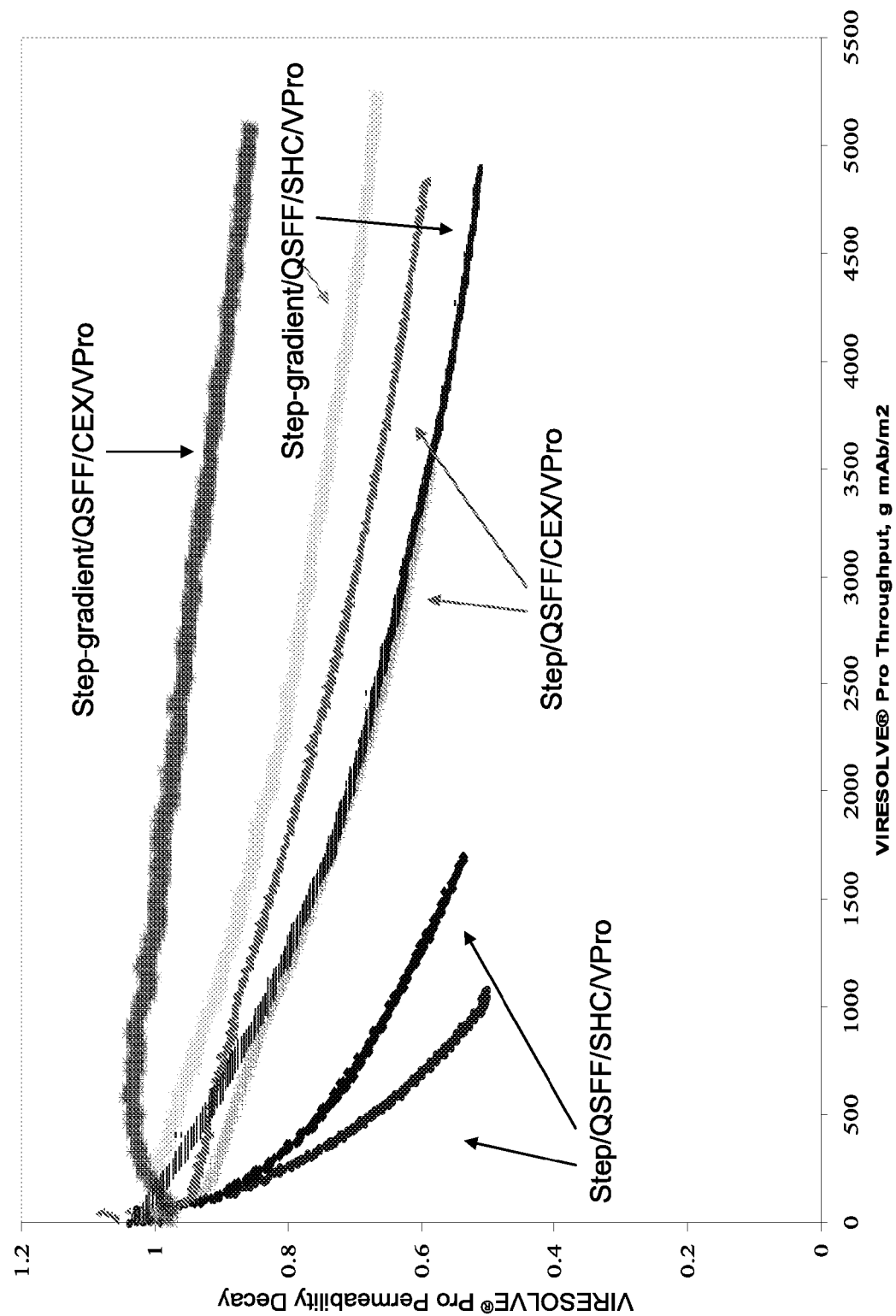
FIG. 14 is a VIRESOLVE® Pro permeability decay graph of anti-VEGF antibody #1 comparing the Protein A pH step-gradient versus the Protein A standard step in terms of facilitating a greater mass throughput over the VIRESOLVE® Pro parvovirus filter. There was about a six-fold increase in mass throughput over the VIRESOLVE® Pro using the protein A pH step-gradient.

The Protein A pH step-gradient was compared to the Protein A standard step (control group, using no pH gradient and eluting protein at or below pH 3.6) in terms of facilitating a greater mass throughput over a parvovirus filter (VIRESOLVE® Pro, Millipore, Inc.). A common HCCF feed was used to run both the Protein A pH step-gradient and Protein A standard step control over the QSFF (Q Sepharose Fast Flow (anion exchange column; GE Healthcare)) in a standard flow through mode before running over the VIRE- SOLVE® Pro parvovirus filter. Several VIRESOLVE® Pro run conditions were tested: 1) Protein A standard step elution pool with the SHC sterile prefilter in-line, 2) Protein A standard step elution with a cation exchange (CEX) membrane adsorber as a prefilter in-line, 3) the Protein A pH step-gradient pool with the SHC prefilter (an uncharged 0.2 micron sterile-grade filter), and 4) the Protein A pH step-gradient pool with a CEX membrane adsorber as a prefilter in-line. Some pools were run with repetition. The VIRESOLVE® Pro was run on a filtration setup that utilizes a set of peristaltic pumps, balances, and pressure sensors to report data into a spreadsheet The pH step-gradient pool with the SHC sterile filter in line performed similarly to the step pool with the cation exchange membrane, both showing around a six-fold increase in possible mass throughput over the VIRESOLVE® Pro. See FIG. 14. Accordingly, this result indicates the unexpected benefit of the protein A pH step-gradient in removing VIRESOLVE® Pro filter foulants without the aid of a CEX membrane prefilter. Additionally, the VIRESOLVE® Pro performance benefited by the combination of the CEX membrane adsorber with the Protein A pH step-gradient pool, leading to an unexpected approximate 18-fold improvement in potential mass throughput as compared to the Protein A standard step elution pool run with the SHC on the VIRESOLVE® Pro.

B. VIRESOLVE® Pro CHOP and SEC Experiments

Samples were taken at different points during the VIRESOLVE® Pro run sequences and assayed for CHOP and SEC. The Protein A standard step sequence with the SHC in line had fairly low CHOP levels, but still contained aggregates. Aggregate levels remained low in the Protein A pH step-gradient experiments through different process steps and resulted in an end pool with less than 1% aggregate. This result was a significant improvement over the pool delivered by the standard step pool. Further, the CHOP levels for the pH step-gradient SHC-VIRESOLVE® Pro pools were comparable to the levels in the standard step run with the cation exchange membrane. The levels were slightly lower than those from the standard step with the SHC. See Tables 4A and 4B. These results show that not only did the pH step-gradient method produced higher mass throughput in comparison to the standard step pool, it also produced comparable or better purity.

TABLE 4A

| | Protein A STEP Elution | | | | | |
| | Experiment 1 | | | Experiment 2 | | |
| HCCF Load CHOP: 1,000,000 ppm | CHOP ppm | Monomer | Aggregate | CHOP ppm | Monomer | Aggregate |
|---|---|---|---|---|---|---|
| Protein A Pool | | | | 1090 | 95.39 | 4.61 |
| QSFF Load | 1000 | 94.01 | 5.99 | 1080 | 94.04 | 5.96 |
| QSFF Pool | 9 | 95.53 | 4.47 | 14 | 95.28 | 4.72 |
| VPro Load | 9 | 95.48 | 4.52 | | | |
| VPro Pool (SHC) | 8 | 95.52 | 4.48 | 12 | 95.29 | 4.71 |
| VPro Pool (CEX Membrane) | 3 | 95.52 | 4.48 | 6 | 95.43 | 4.57 |

TABLE 4B

| | Protein A pH STEP-GRADIENT Elution | | | | | |
| | Experiment 1 | | | Experiment 2 | | |
| HCCF Load CHOP: 1,000,000 ppm | CHOP ppm | Monomer | Aggregate | CHOP ppm | Monomer | Aggregate |
|---|---|---|---|---|---|---|
| Protein A Pool | 800 | 99.28 | 0.72 | 920 | 99.42 | 0.58 |
| QSFF Load | 850 | 98.70 | 1.30 | | | |
| VPro Load | 5 | 99.29 | 0.71 | | | |
| VPro Pool (SHC) | 7 | 99.27 | 0.73 | 6 | 99.32 | 0.68 |
| VPro Pool (CEX Membrane) | | | | <4 | 99.33 | 0.67 |

Example 9

Protein A Full pH Gradient Elution on Protein A

Protein A full pH gradient elution was also tested. All phases and buffers were the same as those used in the pH step-gradient method as described in Example 1, except that 35-60% B as used in the pH step-gradient was decreased to 25-60% at the start of the gradient, which resulted in a higher pH start gradient (starting at about pH 4.6 and ending at about pH 3.7). 25% B correspond to elution buffer pH of 4.58, buffer composition of 18.75 mM acetate and 6.25 mM formate, and buffer conductivity of 1141 uS/cm. 60% B corresponds to elution buffer pH of 3.69, buffer composition of 10 mM acetate and 15 mM formate, and buffer conductivity of 763 uS/cm. See Table 5.

TABLE 5

| Run Phase | Specifics |
|---|---|
| Column Equilibration | Tris buffer, pH 7 |
| Protein Load | Prefiltered HCCF, 14-37 g/L |
| Washes | Various buffers |
| pH Full Gradient Elution | pH Gradient: 25-60% B; A: Acetate, pH 5.0/ B: Formate, pH 2.7 |
| Column Regeneration | NaOH |
| Column Storage | Benzyl alcohol and acetate storage buffer |

Figure 15:
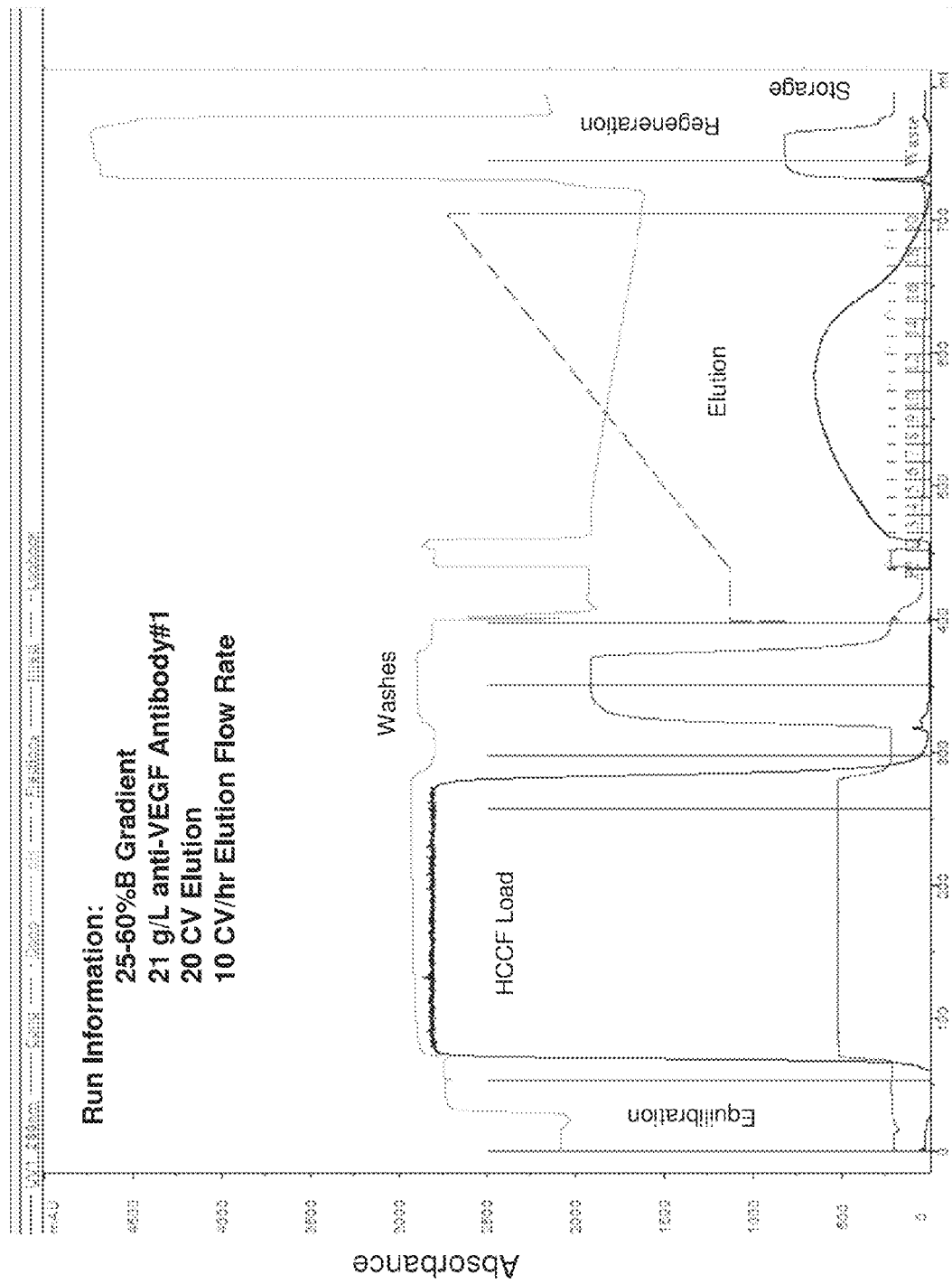
FIG. 15 is a Protein A full pH gradient elution chromatogram showing the actual AKTA UNICORN™ chromatography software traces for the full pH gradient at a load density of 21 g/L. The initial tall UV 250 spike at the start of the gradient is missing, indicating that the pH at the start of the elution is higher than what is required to elute products from the Protein A column.
Figure 16:
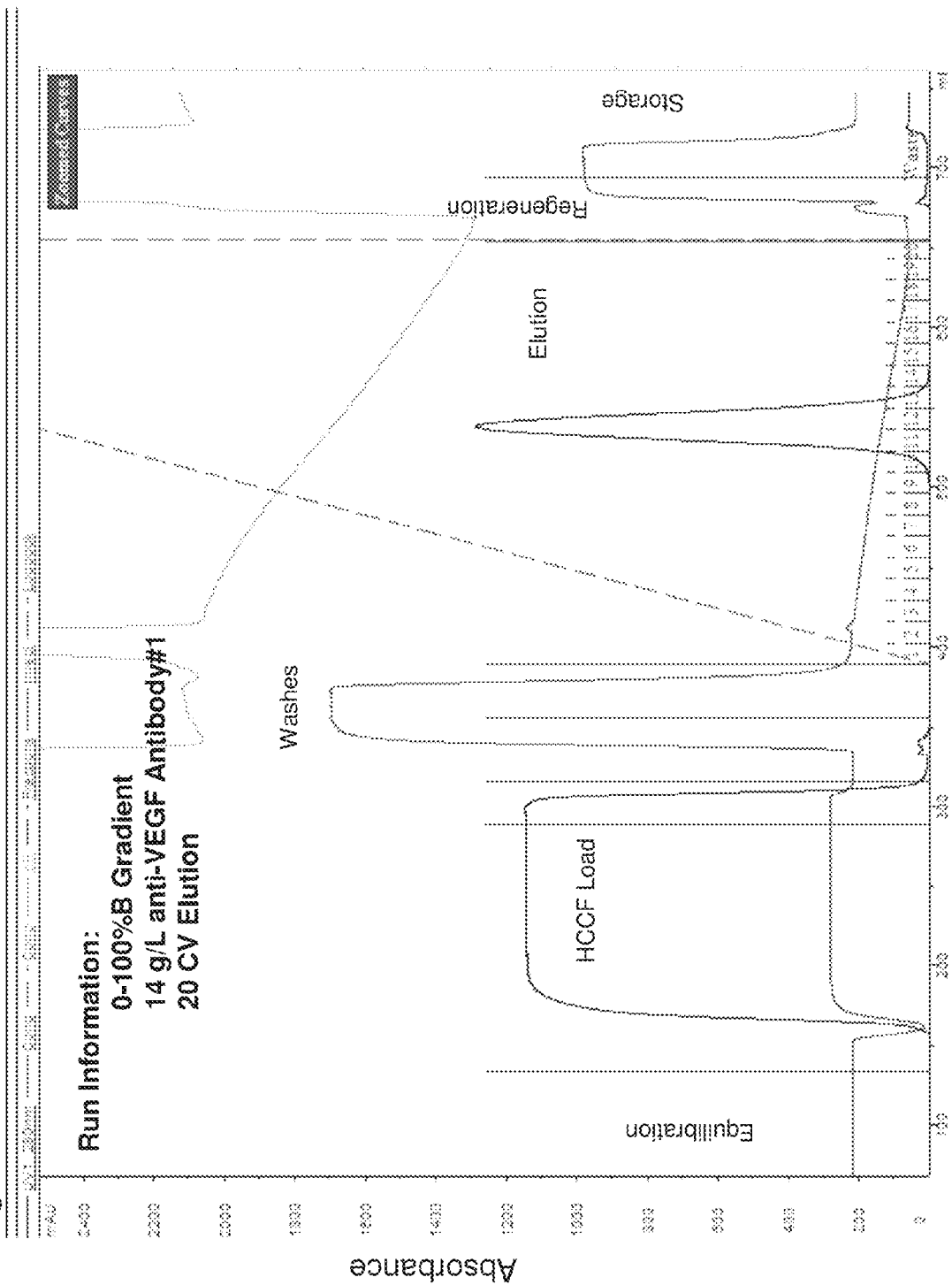
FIG. 16 is a pH 5.0-2.7 pH gradient trial (0-100% B) AKTA chromatogram, indicating that an anti-VEGF antibody #1 elutes as a discrete peak in the range of pH 4.6-3.6.

The elution shape of a full gradient is shown in FIG. 15. All products were eluted by the end of the pH decline. The chromatogram for the full pH gradient is the same in all phases as the pH step-gradient, except that the antibody elution begins at a higher pH. The lack of the initial tall UV 280 spike at the start of the gradient resulted in lower concentration fractions at the beginning of the gradient, with more protein distributed through the rest of the elution phase. This allowed for greater separation of species that elute preferentially at higher pHs than the monomer. Thus, this technique can be equally effective at clearing impurities that separate from the desired product at lower pHs (i.e, the aggregates and CHOPs separated using the step-gradient), with the only drawback as end pool volume as compared to the pH step-gradient (lower fraction concentrations at the start of the gradient translate into a need to pool more fractions together to achieve a mock pool of a desired yield). The SEC traces and integrations for this full gradient also demonstrate separation of aggregate from monomer at the lower pHs, suggesting that benefits and applicability of the pH step-gradient can be extended to a full gradient as well.

Example 10

Aggregate Formation on Protein A Study

To ensure that an aggregate was neither being formed during the low pH or the tail end of the pH step-gradient elution and that the Protein A pH step-gradient technique indeed separated a monomer from an aggregate, rather than causing the formation of an aggregate, purified materials were used to show that aggregate levels of the feed were not increased by processing over Protein A, with or without HCCF components. See Table 6.

TABLE 6

| Protein A Load Material | anti-VEGF antibody #1 HCCF (~pH 7.3) | Protein A pH step-gradient pool, conditioned to pH 7.3 | 50/50 Mix: HCCF flow through + Protein A pH step-gradient pool |
|---|---|---|---|
| Load Monomer | Unknown* | 98.88% | Unknown* |
| Acetic Acid Step Elution Monomer | 95.03% | 99.06% | 99.16% |

*SEC monomer assay not used on HCCF

What is claimed is:

1. A method for purifying a polypeptide comprising a $C_H2/C_H3$ region, comprising the steps of:
   (a) binding the polypeptide to Protein A; and
   (b) eluting the polypeptide with a pH gradient starting at or below 5.0 using an elution buffer, wherein the elution buffer contains a high pH buffer and a low pH buffer and wherein the pH gradient is formed by adjusting a percentage of each pH buffer in the elution buffer,
   wherein the high pH buffer is at about 5.0 and wherein the low pH buffer is at about 2.7, wherein the pH gradient ends at about 3.7, and
   wherein an aggregate, a host cell impurity, a virus filter foulant, a virus particle and a virus-like particle are removed from the desired polypeptide.
2. The method of claim 1, wherein the percentage of low pH buffer starts at about 35%.
3. The method of claim 2, wherein the elution buffer containing the low pH buffer at about 35% comprises about 16.25 mM acetate and about 8.75 mM formate.
4. The method of claim 1, wherein the percentage of low pH buffer starts at about 25%.
5. The method of claim 4, wherein the elution buffer containing the low pH buffer at about 25% comprises about 18.75 mM acetate and 6.25 mM formate.
6. The method of claim 1, wherein the percentage of low pH buffer starts at about 40%.
7. The method of claim 6, wherein the elution buffer containing the low pH buffer at about 40% comprises about 15 mM acetate and 10 mM formate.
8. The method of claim 1, wherein the polypeptide is loaded with a loading density starting at about 14 g/L.
9. The method of claim 1, wherein the Protein A is a Protein A column chromatography resin or a Protein A chromatography sorbent.
10. The method of claim 9, wherein the Protein A chromatography sorbent is a membrane or a monolith.
11. The method of claim 9, wherein the Protein A is a Protein A column chromatography resin and wherein the polypeptide has an elution flow rate ranging from about 5 column volume/hour to about 25 column volume/hour.
12. The method of claim 9, wherein the Protein A is a Protein A column chromatography resin and wherein a purified fraction of the polypeptide contains about or fewer than about 12 Protein A column volumes.
13. The method of claim 1, wherein the pH gradient starts at about pH 4.2.
14. The method of claim 1, wherein the pH gradient starts at about pH 4.3.
15. The method of claim 14, wherein the polypeptide is an anti-VEGF antibody, an anti-CD20 antibody, an anti-MUC16 antibody, an anti-MET antibody or an anti-CD4 antibody.
16. The method of claim 15, wherein the antibody is an anti-VEGF antibody.
17. The method of claim 16, wherein the anti-VEGF antibody is bevacizumab.
18. The method of claim 15, wherein the antibody is an anti-CD20 antibody.
19. The method of claim 18, wherein the anti-CD20 antibody is rituximab.
20. The method of claim 1, wherein the pH gradient starts at about pH 4.6.
21. The method of claim 1, wherein the host cell impurity is Chinese Hamster Ovary Protein (CHOP).
22. The method of claim 1, wherein a basic polypeptide variant is separated from the polypeptide.
23. The method of claim 22, wherein the polypeptide is an anti-VEGF antibody, an anti-CD20 antibody, an anti-MUC16 antibody, an anti-MET antibody or an anti-CD4 antibody.
24. The method of claim 23, wherein the antibody is an anti-VEGF antibody.
25. The method of claim 24, wherein the anti-VEGF antibody is bevacizumab.
26. The method of claim 23, wherein the antibody is an anti-CD20 antibody.
27. The method of claim 26, wherein the anti-CD20 antibody is rituximab.
28. The method of claim 1, wherein the $C_H2/C_H3$ region comprises a Fc region of an immunoglobulin.
29. The method of claim 1, wherein the polypeptide is an antibody.
30. The method of claim 29, wherein the antibody is a monoclonal antibody, a polyclonal antibody, a multi-specific antibody, or an antibody fragment.

31. The method of claim 1, wherein the polypeptide is an immunoadhesion.

32. The method of claim 1, wherein the purified polypeptide has a purity of at least about 98% monomer.

33. The method of claim 32, wherein the polypeptide is an anti-VEGF antibody, an anti-CD20 antibody, an anti-MUC16 antibody, an anti-MET antibody or an anti-CD4 antibody.

34. The method of claim 33, wherein the antibody is an anti-VEGF antibody.

35. The method of claim 34, wherein the anti-VEGF antibody is bevacizumab.

36. The method of claim 33, wherein the antibody is an anti-CD20 antibody.

37. The method of claim 36, wherein the anti-CD20 antibody is rituximab.

38. The method of claim 1, wherein the purified polypeptide has a purity of at least about 99% monomer.

39. The method of claim 38, wherein the polypeptide is an anti-VEGF antibody, an anti-CD20 antibody, an anti-MUC16 antibody, an anti-MET antibody or an anti-CD4 antibody.

40. The method of claim 39, wherein the antibody is an anti-VEGF antibody.

41. The method of claim 40, wherein the anti-VEGF antibody is bevacizumab.

42. The method of claim 39, wherein the antibody is an anti-CD20 antibody.

43. The method of claim 42 wherein the anti-CD20 antibody is rituximab.

44. The method of claim 1, wherein a ratio of a host cell impurity to the purified polypeptide is at least about 20% lower than the ratio in a polypeptide purified by a step elution method, wherein the step elution method comprises binding the polypeptide to Protein A and eluting with a pH starting at or below 3.6.

45. The method of claim 44, wherein the polypeptide is an anti-VEGF antibody, an anti-CD20 antibody, an anti-MUC16 antibody, an anti-MET antibody or an anti-CD4 antibody.

46. The method of claim 45, wherein the antibody is an anti-VEGF antibody.

47. The method of claim 46, wherein the anti-VEGF antibody is bevacizumab.

48. The method of claim 45, wherein the antibody is an anti-CD20 antibody.

49. The method of claim 48, wherein the anti-CD20 antibody is rituximab.

50. The method of claim 1, wherein a ratio of a host cell impurity to the purified polypeptide is at least about 60% lower than the ratio in a polypeptide purified by a step elution method, wherein the step elution method comprises binding the polypeptide to Protein A and eluting with a pH starting at about 3.6.

51. The method of claim 50, wherein the polypeptide is an anti-VEGF antibody, an anti-CD20 antibody, an anti-MUC16 antibody, an anti-MET antibody or an anti-CD4 antibody.

52. The method of claim 51, wherein the antibody is an anti-VEGF antibody.

53. The method of claim 52, wherein the anti-VEGF antibody is bevacizumab.

54. The method of claim 51, wherein the antibody is an anti-CD20 antibody.

55. The method of claim 54, wherein the anti-CD20 antibody is rituximab.

56. The method of claim 44 or 50, wherein the purified polypeptide is a polypeptide monomer.

57. The method of claim 1, wherein the Protein A is a modified or a non-modified Protein A ligand.

58. The method of claim 1, wherein the purification is a manufacturing scale process.

59. The method of claim 1, further comprising subjecting the polypeptide to a virus filtration step.

60. The method of claim 1, further comprising subjecting the polypeptide to an ion exchange chromatography step.

61. The method of claim 60, wherein the ion exchange chromatography step runs continuously after step (b).

62. The method of claim 1, wherein the method does not comprise a further purification step to remove an aggregate.

63. The method of claim 1, wherein the method does not comprise a
further purification step to remove a virus filter foulant.

64. The method of claim 63, wherein the polypeptide is an anti-VEGF antibody, an anti-CD20 antibody, an anti-MUC16 antibody, an anti-MET antibody or an anti-CD4 antibody.

65. The method of claim 64, wherein the antibody is an anti-VEGF antibody.

66. The method of claim 65, wherein the anti-VEGF antibody is bevacizumab.

67. The method of claim 64, wherein the antibody is an anti-CD20 antibody.

68. The method of claim 67, wherein the anti-CD20 antibody is rituximab.

69. The method of claim 1, wherein the polypeptide is an anti-VEGF antibody, an anti-CD20 antibody, an anti-MUC16 antibody, an anti-MET antibody or an anti-CD4 antibody.

70. The method of claim 69, wherein the antibody is an anti-VEGF antibody.

71. The method of claim 70, wherein the anti-VEGF antibody is bevacizumab.

72. The method of claim 69, wherein the antibody is an anti-CD20 antibody.

73. The method of claim 72, wherein the anti-CD20 antibody is rituximab.

* * * * *